US007692045B2

(12) United States Patent
Teles et al.

(10) Patent No.: US 7,692,045 B2
(45) Date of Patent: Apr. 6, 2010

(54) METHOD FOR PURIFYING AND CONCENTRATING DINITROGEN MONOXIDE

(75) Inventors: Joaquim Henrique Teles, Otterstadt (DE); Beatrice Roessler, Bad Duerkheim (DE); Thomas Genger, Lambsheim (DE); Andreas Glass, Ruhland (DE); Dieter Baumann, Frankenthal (DE); Jan-Martin Loening, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 201 days.

(21) Appl. No.: 11/575,914

(22) PCT Filed: Sep. 22, 2005

(86) PCT No.: PCT/EP2005/010267

§ 371 (c)(1),
(2), (4) Date: Mar. 23, 2007

(87) PCT Pub. No.: WO2006/032502

PCT Pub. Date: Mar. 30, 2006

(65) Prior Publication Data

US 2008/0255393 A1 Oct. 16, 2008

(30) Foreign Application Priority Data

Sep. 23, 2004 (DE) ........................ 10 2004 046 167

(51) Int. Cl.
C07C 45/27 (2006.01)
C07B 41/06 (2006.01)
C01B 21/22 (2006.01)
(52) U.S. Cl. ........................ 568/408; 568/952; 423/400
(58) Field of Classification Search ................ 568/408, 568/952; 423/400
See application file for complete search history.

(56) References Cited

U.S. PATENT DOCUMENTS

| 2,636,898 | A |   | 4/1953 | Buckley |
| 3,063,986 | A |   | 11/1962 | Wilke et al. |
| 3,656,899 | A |   | 4/1972 | Baechle et al. |
| 3,804,914 | A |   | 4/1974 | Fahey |
| B316,917 | I5 |  | 1/1975 | Fahey |
| 3,925,494 | A |   | 12/1975 | Fahey |
| 4,139,595 | A | * | 2/1979 | Vaseen ........................ 423/393 |
| 4,177,645 | A |   | 12/1979 | Schwarz |
| 4,376,105 | A | * | 3/1983 | Matuda et al. ............... 423/400 |
| 4,844,715 | A |   | 7/1989 | Henrich et al. |
| 5,128,296 | A |   | 7/1992 | Matson et al. |
| 5,177,278 | A |   | 1/1993 | Sanchez |
| 5,180,870 | A |   | 1/1993 | Paciello |
| 5,210,349 | A |   | 5/1993 | Matson et al. |
| 5,321,176 | A |   | 6/1994 | Sanchez |
| 5,401,884 | A |   | 3/1995 | Diercks et al. |
| 5,849,257 | A |   | 12/1998 | Fujiwara et al. |
| 6,194,624 | B1 |  | 2/2001 | Pinkos |
| 6,370,911 | B1 |  | 4/2002 | Zhou et al. |
| 6,387,161 | B1 |  | 5/2002 | Zhou et al. |
| 6,505,482 | B2 |  | 1/2003 | Zhou et al. |
| 7,070,746 | B1 | * | 7/2006 | Notte et al. ................. 423/219 |
| 7,105,704 | B2 |  | 9/2006 | Panov et al. |
| 2005/0203316 | A1 | | 9/2005 | Panov et al. |
| 2006/0106258 | A1 | | 5/2006 | Panov et al. |
| 2006/0281952 | A1 | | 12/2006 | Teles et al. |

FOREIGN PATENT DOCUMENTS

| DE | 2 040 219 | | 3/1971 |
| DE | 25 19 817 | A1 | 11/1976 |
| DE | 27 32 267 | | 1/1979 |
| DE | 37 08 469 | A1 | 9/1988 |
| DE | 196 05 211 | A1 | 8/1997 |
| DE | 198 56 682 | A1 | 6/2000 |
| DE | 103 19 489 | A1 | 11/2004 |
| DE | 103 44 594 | A1 | 5/2005 |
| DE | 103 44 595 | A1 | 5/2005 |
| EP | 0 285 420 | A1 | 10/1988 |
| EP | 0 624 565 | A1 | 11/1994 |
| EP | 1 076 217 | A2 | 2/2001 |
| GB | 649 680 | | 1/1951 |
| GB | 1 327 401 | | 8/1973 |
| GB | 1 551 741 | | 8/1979 |
| JP | 2000-53597 | | 2/2000 |
| WO | WO 98/25698 | | 6/1998 |
| WO | WO 00/01654 | | 1/2000 |
| WO | WO 00/73202 | A1 | 12/2000 |
| WO | WO 03/078370 | A1 | 9/2003 |

(Continued)

OTHER PUBLICATIONS

A. S. Noskov, et al., "Ammonia oxidation into nitrous oxide over Mn/Bi/Al catalyst I. Single cooling tube experiments", Chemical Engineering Journal, vol. 91, 2003, pp. 235-242.

Gennady I. Panov, et al., "Non-Catalytic Liquid Phase Oxidation of Alkenes with Nitrous Oxide. 1. Oxidation of Cyclohexene to Cyclohexanone". React. Kinet. Catal. Lett., vol. 76, No. 2, 2002, pp. 401-406.

Konstantin A. Dubkov, et al., "Non-Catalytic Liquid Phase Oxidation of Alkenes with Nitrous Oxide. 2 Oxidation of Cyclopentene to Cyclopentanone", React. Kinet. Catal. Lett., vol. 77, No. 1, 2002, pp. 197-205.

(Continued)

Primary Examiner—Sikarl A Witherspoon
(74) Attorney, Agent, or Firm—Oblon, Spivak, McClelland, Maier & Neustadt, L.L.P.

(57) ABSTRACT

The present invention relates to a process for purifying a gas mixture comprising dinitrogen monoxide and to the use of a gas mixture purified in this way as an oxidant for olefins. In a further embodiment, the present invention also relates to a process for preparing ketones comprising the oxidation of an olefin with a gas mixture which has been purified in accordance with the invention and comprises dinitrogen monoxide.

22 Claims, No Drawings

FOREIGN PATENT DOCUMENTS

| WO | WO 03/078371 A1 | 9/2003 |
|---|---|---|
| WO | WO 03/078372 A1 | 9/2003 |
| WO | WO 03/078374 A1 | 9/2003 |
| WO | WO 03/078375 A1 | 9/2003 |
| WO | WO 2004/000777 A1 | 12/2003 |
| WO | WO 2005/030689 A2 | 4/2005 |
| WO | WO 2005/030690 A2 | 4/2005 |

OTHER PUBLICATIONS

E. V. Starokon, et al., "Liquid phase Oxidation of Alkenes with Nitrous Oxide to Carbonyl Compounds", Adv. Synth. Catal. 2004, pp. 268-274.

M. Thiemann, et al., "Ullmann's Encyclopedia of Industrial Chemistry", 6th edition, electronic realese, Chapter "Nitric Acid, Nitrous Acid, and Nitrogen Oxides", vol. 23, section. 1.4.2.3, 1 front page, pp. 36-40.

Anthony K. Uriarte, "Nitrous Oxide ($N_2O$)—Waste to Value", Studies in Surface Science and Catalysis, 130, 2000, pp. 743-748.

J. Wolf, et al., "Ullmann's Encyclopedia of Industrial Chemistry", 6th edition, electronic realese, Chapter "Air", Section 7.2.3.1, vol. 1, 2000, 1 front page, pp. 704-706.

Darryl R. Fahey, "Selective Hydrogenation of 1,5,9-Cyclododecatriene to Cyclododecene Catalyzed by Ruthenium Complexes", J. Org. Chem., vol. 38, No. 1, 1973, pp. 80-87.

T. Schiffer, et al., "Cyclododecatriene, Cyclooctadiene, and 4-Vinylcyclohexene", Ullman's Encyclopedia of Industrial Chemistry, 6th Edition, 2000, Electronic Release, vol. 10, WileyVCH, 1 front page, pp. 267-270.

H. Weber, et al., "Zur Bildungsweise von cis, trans, trans-Cyclododecatrien-(1.59) mittels Titanhaltiger Ziegler-Katalysatoren", Liebigs Ann. Chem. 681, 1965, pp. 10-20.

* cited by examiner

METHOD FOR PURIFYING AND CONCENTRATING DINITROGEN MONOXIDE

The present invention relates to a process for purifying a gas mixture comprising dinitrogen monoxide and to the use of a gas mixture purified in this way as an oxidant for olefins. In a further embodiment, the present invention also relates to a process for preparing ketones comprising the oxidation of at least one olefin with a gas mixture which has been purified in accordance with the invention and comprises dinitrogen monoxide.

The prior art discloses various preparative processes for dinitrogen monoxide. It is likewise known that dinitrogen monoxide can be used, for example, as an oxidant for olefins.

For instance, WO 98/25698 discloses a process for preparing dinitrogen monoxide by catalytic partial oxidation of NH3 with oxygen. According to WO 98/25698, a catalyst composed of manganese oxide, bismuth oxide and aluminum oxide is used, which leads to dinitrogen monoxide with high selectivity. A similar catalyst system is also described in detail in a scientific study (Noskov et al., *Chem. Eng. J.* 91 (2003) 235-242). U.S. Pat. No. 5,849,257 likewise discloses a process for preparing dinitrogen monoxide by oxidation of ammonia. The oxidation takes place in the presence of a copper-manganese oxide catalyst.

In the process disclosed in WO 00/01654, dinitrogen monoxide is prepared by reducing a gas stream comprising $NO_x$ and ammonia.

The oxidation of an olefinic compound to an aldehyde or a ketone by means of dinitrogen monoxide is described, for example, in GB 649,680 or U.S. Pat. No. 2,636,898 which is equivalent thereto. Both documents quite generally disclose that the oxidation can in principle be effected in the presence of a suitable oxidation catalyst.

The more recent scientific articles of G. L. Panov et al., "Non-Catalytic Liquid Phase Oxidation of Alkenes with Nitrous Oxide. 1. Oxidation of Cyclohexene to Cyclohexanone", React. Kinet. Catal. Lett. Vol. 76, No. 2 (2002) p. 401-405, and K. A. Dubkov et al., "Non-Catalytic Liquid Phase Oxidation of Alkenes with Nitrous Oxide. 2. Oxidation of Cyclopentene to Cyclopentanone", React. Kinet. Catal. Lett. Vol. 77, No. 1 (2002) p. 197-205 likewise describe oxidations of olefinic compounds with dinitrogen monoxide. A scientific article "Liquid Phase Oxidation of Alkenes with Nitrous Oxide to Carbonyl Compounds" by E. V. Starokon et al. in *Adv. Synth. Catal.* 2004, 346, 268-274 also includes a mechanistic study of the oxidation of alkenes with dinitrogen monoxide in the liquid phase.

The synthesis of carbonyl compounds from alkenes with dinitrogen monoxide is also described in various international patent applications. For instance, WO 03/078370 discloses a process for preparing carbonyl compounds from aliphatic alkenes with dinitrogen monoxide. The reaction is carried out at temperatures in the range from 20 to 350° C. and pressures of from 0.01 to 100 atm. WO 03/078374 discloses a corresponding process for preparing cyclohexanone. According to WO 03/078372, cyclic ketones having from 4 to 5 carbon atoms are prepared. According to WO 03/078375, cyclic ketones are prepared under these process conditions from cyclic alkenes having from 7 to 20 carbon atoms. WO 03/078371 discloses a process for preparing substituted ketones from substituted alkenes. WO 04/000777 discloses a process for preparing di- and polyalkenes with dinitrogen monoxide to give the corresponding carbonyl compounds. The purification of dinitrogen monoxide is not mentioned in these documents.

It is likewise known that off gas streams comprising dinitrogen monoxide can be used for further reactions. Dinitrogen monoxide is obtained as an undesired by-product in various chemical processes, especially in oxidations with nitric acid and there very particularly in the oxidation of cyclohexanone and/or cyclohexanol to adipic acid. Other examples of processes in which dinitrogen monoxide is obtained as an undesired by-product are the oxidation of cyclododecanone and/or cyclododecanol with nitric acid to give dodecanedicarboxylic acid and the partial oxidation of $NH_3$ to NO.

For instance, DE 103 44 595.1, DE 103 44 594.3 and DE 103 19 489.4 disclose processes for oxidizing olefins with dinitrogen monoxide, specifically the oxidation of cyclododecatriene, of cyclododecene and of cyclopentene. All three applications disclose that, in addition to other dinitrogen monoxide sources, it is also possible to use off gas streams which can be purified, for example, by distillative methods before they are used as oxidants.

Both in the preparation of dinitrogen monoxide and in the use of offgas streams, $N_2O$ is obtained initially as a dilute gaseous mixture with other components. These components can be divided into those which have a disruptive effect for specific applications and those which behave inertly. For use as an oxidant, gases having a disruptive effect include $NO_x$ or, for example, oxygen. The term "$NO_x$", as understood in the context of the present invention, refers to all compounds $N_aO_b$ where a is 1 or 2 and b is a number from 1 to 8, except $N_2O$. Instead of the term "$NO_x$", the term "nitrogen oxides" is also used in the context of the present invention. Disruptive secondary components also include $NH_3$ and organic acids.

For specific applications, it is necessary to purify the dinitrogen monoxide used before the reaction. For example, for the use of dinitrogen monoxide as an oxidant, it is necessary to remove disruptive secondary components such as oxygen or nitrogen oxides $NO_x$.

Processes for removing $NO_x$ are known in principle from the prior art. A review is given, for example, by M. Thiemann et. al in Ullmann's Encyclopedia, 6th Edition, 2000, Electronic Edition, Chapter "Nitric Acid, Nitrous Acid, and Nitrogen Oxides", Section 1.4.2.3.

The application WO 00/73202 describes a method as to how $NO_x$ and $O_2$ can be removed from an $N_2O$-containing gas stream. The $NO_x$ is removed by catalytic reduction with $NH_3$ and oxygen by catalytic reduction with hydrogen or other reducing agents. However, this method has the disadvantage that the product is contaminated with $NH_3$. A high depletion of oxygen (for example to more than 90% of the original amount) is possible only when a loss of $N_2O$ is accepted (of from 3 to 5% of the amount originally present).

For specific applications, it may be necessary also to remove the inert compounds, since they can slow the desired reduction with $N_2O$ by dilution. The term "inert gas", as used in the context of the present invention, refers to a gas which behaves inertly with regard to the reaction of $N_2O$ with an olefin, i.e. reacts under the conditions of the reaction of olefins with $N_2O$ neither with the olefins nor with $N_2O$. Inert gases include, for example, nitrogen, carbon dioxide, carbon monoxide, hydrogen, argon, methane, ethane and propane. However, the inert gases lower the space-time yield, so that a depletion is likewise advantageous.

DE 27 32 267 A1 discloses, for example, a process for purifying dinitrogen monoxide, wherein nitrogen oxide, nitrogen dioxide, carbon dioxide and water are initially removed and the gas mixture is subsequently liquefied by compression to from 40 to 300 bar and cooling to from 0 to −88° C. From this liquefied gas mixture, dinitrogen monoxide is then removed. Although this method achieves a purification and concentration of the $N_2O$, it is economically unattractive owing to the required high pressure (60 bar), the low temperatures (−85° C.) and the associated high capital costs.

U.S. Pat. No. 4,177,645 discloses a process for removing dinitrogen monoxide from offgas streams which likewise comprises a prepurification and a low temperature distillation. The application EP 1 076 217 A1 likewise describes a method for removing low-boiling impurities from $N_2O$ by low temperature distillation.

U.S. Pat. No. 6,505.482, U.S. Pat. No. 6,370,911 and U.S. Pat. No. 6,387,161 also disclose processes for purifying dinitrogen monoxide, in which a low temperature distillation is in each case carried out in a special plant.

However, as a result of the high pressures and low temperatures, a low temperature distillation entails high apparatus demands, which make the purification of the dinitrogen monoxide with such a process inconvenient and costly. Particularly troublesome in this context is the fact that the melting point of $N_2O$ at standard pressure is only 3K below the boiling point. It is therefore necessary to employ high pressures.

DT 20 40 219 discloses a preparative process for dinitrogen monoxide, wherein the dinitrogen monoxide obtained is concentrated and purified after the synthesis. According to DT 20 40 219, dinitrogen monoxide is prepared initially by oxidizing ammonia. The dinitrogen monoxide prepared is purified by separating the oxidized gases and concentrating by-absorption under high pressure, which is followed by a desorption under reduced pressure. Secondary components are removed, for example, by treatment with an alkali solution. According to DT 20 40 219, water is used as the solvent for the absorption of the gas mixture.

It is possible with the process disclosed DT 20 40 219 to separate the different nitrogen oxides, but the process entails the use of large amounts of solvent and/or high pressures for the absorption owing to the low solubility of $N_2O$ in water. This leads to the plants used also having to be designed for large volumes. This makes the process uneconomic overall.

Starting from this prior art, it is an object of the present invention to provide a process by which dinitrogen monoxide-containing streams can be purified and concentrated effectively and inexpensively, i.e. disruptive and inert components can simultaneously be removed. Dinitrogen monoxide purified in this way is required in particular as an oxidant.

According to the invention, this object is achieved via a process for purifying a gas mixture comprising dinitrogen monoxide, at least comprising the following steps:

A1 Absorption, of the gas mixture in an organic solvent
A2 Desorption of the gas mixture from the laden organic solvent
B Adjusting the content of nitrogen oxides $NO_x$ in the gas mixture to at most 0.5% by volume based on the total volume of the gas mixture.

One advantage of the process according to the invention is that not only the destructive components but also the inert components are removed. The dinitrogen monoxide purified in accordance with the invention is thus simultaneously concentrated. Dinitrogen monoxide purified in this way may be used, especially in liquid form, advantageously as an oxidant, since no further inert compounds enlarge the reaction volume and slow the reaction.

The gas mixture comprising dinitrogen monoxide which is used may in principle stem from any source.

The term "gas mixture" as used in the context of the present invention, refers to a mixture of two or more compounds which are in the gaseous state at ambient pressure and ambient temperature. At altered temperature or altered pressure, the gas mixture may also be present in another state of matter, for example liquid, and is still referred to as a gas mixture in the context of the present invention.

When a gas mixture is used, its content of dinitrogen monoxide is substantially arbitrary, as long as it is guaranteed that the inventive purification is possible.

The $N_2O$-containing gas mixtures which are used for this process generally have an $N_2O$ content between 2 and 80% by volume of $N_2O$. It also contains, for example, from 2 to 21% by volume of $O_2$ and up to 30% by volume of $NO_x$ as undesired components. In addition, it may also contain varying amounts of $N_2$, $H_2$, $CO_2$, CO, $H_2O$, $NH_3$; traces of nitric acid and organic compounds may also be present.

In the context of the present invention, the composition of the gas mixtures or of the liquefied gas mixtures is specified in % by volume. The data relate to the composition of the gas mixtures at ambient pressure and ambient temperature.

In a preferred embodiment of the process according to the invention, a gas mixture containing at least 5% by volume of dinitrogen monoxide is used, but preference is given in turn to using mixtures having a dinitrogen monoxide content in the range from 6 to 80% by volume, more preferably in the range from 7 to 60% by volume and especially preferably in the range from 8 to 50% by volume.

In principle, the composition of the mixtures may be determined in the context of the present invention in any way known to those skilled in the art. The composition of the gas mixtures is determined in the context of the present invention preferably by gas chromatography. However, it may also be determined by means of UV spectroscopy. IR spectroscopy or by wet chemical methods.

In a preferred embodiment of the present invention, the gas mixture comprising dinitrogen monoxide is at least one dinitrogen monoxide-containing off gas of a chemical process. The scope of the present invention also embraces embodiments in which at least two nitrogen monoxide-containing offgases of a single plant serve as the gas mixture comprising dinitrogen monoxide. Equally embraced are embodiments in which at least one dinitrogen monoxide-containing off gas of one plant and at least one further dinitrogen monoxide-containing off gas of at least one further plant serve as the gas mixture comprising dinitrogen monoxide.

Accordingly, the present invention also relates to a process as described above, wherein the gas mixture comprising dinitrogen monoxide is at least one dinitrogen monoxide-containing offgas of at least one industrial process.

The term "gas mixture comprising dinitrogen monoxide" refers in the context of the present invention both to embodiments in which the offgas mentioned is subjected to the inventive purification process in unmodified form and to embodiments in which at least one of the offgases mentioned is subjected to a modification.

The term "modification" as used in this context within the scope of the present invention refers to any suitable process by which the chemical composition of a gas mixture is altered. Accordingly, the term "modification" embraces, inter alia, embodiments in which a dinitrogen monoxide-containing offgas is concentrated with regard to the dinitrogen monoxide content in at least one suitable process. Preference is given to not subjecting the offgas to any modification.

In a further embodiment, the chemical composition of an offgas may also be altered by adding pure dinitrogen monoxide to the offgas.

The gas mixture comprising $N_2O$ which is used may, for example, be an offgas from an industrial process. It preferably stems from an offgas of a plant for preparing carboxylic acids by oxidation of alcohols or ketones with nitric acid, for example from an adipic acid or dodecanedicarboxylic acid plant, from the offgas of a nitric acid plant which uses the above offgas streams as a reactant, from the offgas of a plant for the partial oxidation of NH$_3$ or from the offgas of a plant which uses the gas mixtures generated therein, for example a hydroxylamine plant.

According to the invention, it is also possible to use a mixture of different offgases.

In a more preferred embodiment of the present invention, the at least one dinitrogen monoxide-containing offgas stems from an adipic acid plant, a dodecanedioic acid plant, a hydroxylamine plant and/or a nitric acid plant, the latter in turn preferably being operated with at least one offgas of an adipic acid plant, of a dodecanedioic acid plant or of a hydroxylamine plant.

In a preferred embodiment, the offgas stream of an adipic acid plant is used, in which generally from 0.8 to 1.0 mol of N$_2$O is formed per mole of adipic acid formed by oxidation of cyclohexanol/cyclohexanone mixtures with nitric acid. As described, for example, in A. K. Uriarte et al., Stud. Surf. Sci. Catal. 130 (2000) p. 743-748, the offgases of adipic acid plants also contain different concentrations of further constituents including nitrogen, oxygen carbon dioxide, carbon monoxide, nitrogen oxides, water and volatile organic compounds, The abovementioned dodecanedioic acid plant is substantially of an identical or plant type.

An example of a typical composition of an offgas of an adipic acid plant or of a dodecanedioic acid plant is reproduced in the following table:

| Component | Concentrations/% by wt. |
|---|---|
| NO$_x$ | 19-25 |
| N$_2$O | 20-28 |
| N$_2$ | 30-40 |
| O$_2$ | 7-10 |
| CO$_2$ | 2-3 |
| H$_2$O | ~7 |

The offgas stream of an adipic acid plant or of a dodecanedioic acid plant may be used directly in the process according to the invention.

In a likewise preferred embodiment, the offgas stream of a nitric acid plant is used which is fed fully or partly with offgases comprising dinitrogen monoxide and nitrogen oxides from other processes. In such nitric acid plants, nitrogen oxides are adsorbed and for the most part converted to nitric acid, while dinitrogen monoxide is not converted. For example, such a nitric acid plant may be supplied by nitrogen oxides which are prepared by selective combustion of ammonia and by offgases of an adipic acid plant and/or by offgases of a dodecanedioic acid plant. It is equally possible to supply such a nitric acid plant solely by offgases of an adipic acid plant and/or by offgases of a dodecanedioic acid plant.

The offgases of such nitric acid plants always contain varying concentrations of still further constituents including nitrogen, oxygen, carbon dioxide, carbon monoxide, nitrogen oxides, water and volatile organic compounds.

An example of a typical composition of an offgas of such a nitric acid plant is reproduced in the following table:

| Component | Concentrations/% by wt. |
|---|---|
| NO$_x$ | <0.1 |
| N$_2$O | 8-36 |
| N$_2$ | 57-86 |
| O$_2$ | 3-9 |
| CO$_2$ | 1-4 |
| H$_2$O | ~0.6 |

The offgas stream of a nitric acid plant may be used directly in the process according to the invention.

In a likewise preferred embodiment of the process according to the invention, the offgas stream of a hydroxylamine plant is used, in which, for example, ammonia is initially oxidized with air or oxygen to give NO, and small amounts of dinitrogen monoxide are formed as a by-product. The NO is subsequently hydrogenated with hydrogen to give hydroxylamine. Since dinitrogen monoxide is inert under the hydrogenation conditions, it accumulates in the hydrogen circuit. In preferred process versions, the purge stream of a hydroxylamine plant contains dinitrogen monoxide in the range from 9 to 13% by volume in hydrogen. This purge stream may be used as such for the inventive purification. It is equally possible to concentrate this stream in a suitable manner with regard to the dinitrogen monoxide content as described above.

Accordingly, the present invention also relates to a process as described above, wherein the gas mixture comprising dinitrogen monoxide is the offgas of an adipic acid plant and/or of a dodecanedioic acid plant and/or of a hydroxylamine plant and/or of a nitric acid plant operated with the offgas of an adipic acid plant and/or of a dodecanedioic acid plant and/or of a hydroxylamine plant.

It is equally possible in the context of the present invention to selectively prepare dinitrogen monoxide for use in the process. Preference is given inter alia to the preparation via the thermal decomposition of NH$_4$NO$_3$, as described, for example, in U.S. Pat. No. 3,656,899, whose contents on this subject are incorporated by reference fully into the context of the present application. Preference is likewise further given to the preparation via the catalytic oxidation of ammonia, as described, for example, in U.S. Pat. No. 5,849,257 or in WO 98/25698, whose contents of this subject are incorporated by reference fully into the context of the present application.

The desired product contains at least 50% by volume of N$_2$O, more preferably at least 60% by volume of N$_2$O and most preferably at least 75% by volume of N$_2$O. At the same time, the product contains less than 1% by volume of O$_2$, in particular less than 0.5% by volume of O$_2$, less than 0.5% by volume of NO$_x$ and less than 1% by volume of NH$_3$.

The N$_2$O concentration is effected in accordance with the invention by selective absorption of N$_2$O from the crude gas mixture in a suitable organic solvent and subsequent desorption of N$_2$O from the laden solvent in step A1 and A2.

Suitable solvents for the absorption in step A1 are those which have a better solubility for N$_2$O than for the undesired components of the entering reactant gas.

According to the invention, the organic solvents used may be any solvents in which the ratio between N$_2$O solubility (in mol/mol of solvent) and the solubility of the undesired secondary components under the conditions prevailing in the absorber (this ratio is referred to hereinbelow as □) is at least 5. This ratio may be determined for each individual component present in the gas mixture. Preferred organic solvents have, for example at 30° C., a □$_{O2}$ value of from 6 to 30, preferably from 9 to 25, and a □$_{N2}$ value of greater than 10, preferably of greater than 20, in particular of greater than 30.

Examples of suitable solvents are, for example, aliphatic hydrocarbons, preferably having at least 5 carbon atoms, more preferably having at least 8 carbon atoms, substituted or unsubstituted aromatic hydrocarbons, esters, ethers, amides, lactones, lactams, nitriles, alkyl halides, olefins or mixtures of these solvents.

According to the invention, very particular preference is given to solvents which have a boiling point at standard pressure of at least 100° C., since this reduces the solvent losses both in the offgas stream of the absorber and of the desorber.

In addition, solvents suitable in accordance with the invention simultaneously have a good solubility for dinitrogen monoxide. The solubility is specified by the ratio between the partial pressure of $N_2O$ in the gas phase and the proportion by weight of $N_2O$ in the liquid phase (Henry coefficient, $H_{N2O}$), i.e. a small value means a high solubility of dinitrogen monoxide in the solvent. This ratio for an organic solvent used in accordance with the invention at 30° C. is preferably less than 1000, more preferably less than 750, particularly preferably less than 500, in particular less than 260.

Suitable solvents include N-methylpyrrolidone, dimethylformamide, dimethyl sulfoxide, propylene carbonate, sulfolane, N,N-dimethylacetamide or cyclopentane. Particular preference is given in the context of the present invention, for example, to toluene, nitrobenzene, 1,2-dichlorobenzene, tetradecane, for example a technical-grade mixture of saturated hydrocarbons having predominantly 14 carbon atoms, and dimethyl phthalate.

In a preferred embodiment, the present invention therefore relates to a process for purifying a gas mixture comprising dinitrogen monoxide as described above, wherein the organic solvent used in step A1 is selected from a group consisting of toluene, nitrobenzene, 1,2-dichlorobenzene, tetradecane and dimethyl phthalate.

The absorption in step A1 of the process according to the invention may in principle be effected by all processes known to those skilled in the art. In particular, the absorption of $N_2O$ in the solvent may be brought about by increasing the pressure of the reactant gas or by lowering the temperature of the solvent or by a combination of the methods mentioned.

According to the invention, the absorption is effected in units (absorbers) in which a gas-liquid phase interface is generated, through which mass and heat transfer between the phases is enabled, and which are provided if required with internal or external equipment for heat supply and/or heat removal.

The phases can be conducted in the absorber in cocurrent, in countercurrent or a combination thereof.

According to the invention, the absorption may be carried out in one or more stages.

Possible embodiments of the absorber are columns having trays, for example double-cap trays or sieve trays, columns having structured internals, for example structured packings, columns having unstructured internals, for example random packings, or apparatus in which the liquid phase is present in dispersed form, for example by spraying in nozzles, or a combination thereof.

The desorption of $N_2O$ from the laden solvent in step A2 of the process according to the invention may be brought about by pressure reduction via the solvent, temperature increase of the solvent or by stripping with solvent vapor or a combination thereof.

The demands on the units (desorbers) for the desorption of $N_2O$ from the laden solvent, and the conduction of the phases, are analogous to those of the absorber, i.e. suitable units are those in which a gas-liquid phase interface is generated, through which heat and mass transfer between the phases is enabled, and which are equipped if required with internal or external equipment for heat supply and/or heat removal.

According to the invention, the desorption may be carried out in one or more stages.

Possible embodiments of the desorber are a simple (flash) vessel and columns.

A preferred embodiment of the present invention in which the absorption and desorption are combined in one apparatus is the dividing wall column. In this column, the absorption and desorption are operated in countercurrent in several stages by temperature change, combined with a stripping with solvent vapor.

In a preferred embodiment, the present invention therefore relates to a process as described above, wherein steps A1 and A2 are carried out in a dividing wall column.

In a particularly preferred embodiment of the invention, in step A1, the gas mixture comprising $N_2O$ is initially absorbed under elevated pressure $p_{abso}$ in an absorption column operated in countercurrent and having random packing, and transferred in step A2 into a vessel in which the $N_2O$-laden solvent is decompressed to a lower pressure $p_{deso} < p_{abso}$. The process is preferably operated virtually isothermally with a temperature differential between absorption and desorption temperature of not more than 20K, preferably not more than 15K, in particular not more than 10K. The absorption pressure is from 1 to 100 bar, preferably from 5 to 65 bar, in particular from 10 to 40 bar, and the desorption pressure from 0.1 to 2 bar, preferably from 0.5 to 1.5 bar, more preferably from 1.0 to 1.2 bar.

A further embodiment of the invention relates to a process in which two or more dinitrogen monoxide concentration stages comprising steps A1 and A2 are carried out successively.

In this case, the gas desorbed in the stage i-1 serves as the reactant gas of the subsequent stage i. Particular preference is given in the context of the invention to a two-stage embodiment.

The solvent may be identical for all stages. Alternatively, different solvents may be used in different stages.

The present invention therefore relates in a further embodiment to a process as described above, which comprises a plurality of steps A1 and A2.

The process according to the invention further comprises a step B, wherein the content of nitrogen oxides in the gas mixture is adjusted to at most 0.5% by volume based on the total volume of the gas mixture.

It is possible in the context of the present invention to carry out step B before or after steps A1 and A2. The present invention therefore relates in one embodiment to a process as described above, wherein steps A1 A2 are performed before step B. In an alternative embodiment, the present invention relates to a process as described above, wherein step B is performed before steps A1 and A2.

It is equally possible in the context of the present invention that the process comprises a plurality of steps B. It is thus also possible, for example, to carry out a step B before steps A1 and A2 and a further step B after steps A1 and A2.

In principle, all suitable processes for removing $NO_x$ are useful for step B of the process according to the invention. Suitable processes are, for example, the catalytic reduction with hydrocarbons or ammonia, the catalytic decomposition over suitable catalysts, absorption in strongly oxidizing solutions and the absorption in acidic or alkaline solutions.

Suitable oxidizing solutions in the context of the present invention are, for example, solutions of hydrogen peroxide. According to the invention, suitable strongly acidic solutions are solutions comprising nitric acid or sulfuric acid. According to the invention, suitable alkaline solutions are, for example, solutions comprising hydroxides or carbonates, for example sodium hydroxide or sodium carbonate. Suitable liquids for this scrubbing, in addition to those already mentioned, are in particular those which are familiar to those skilled in the art for the removal of $NO_x$ from offgases. Suitable scrubbing solutions or suspensions are, for example, aqueous solutions or suspensions comprising magnesium carbonate, magnesium hydroxide, solutions of vanadium in nitrous acid, ammonium sulfide and ammonium bisulfide, limewater, ammonia, hydrogen peroxide and in particular solutions comprising sodium carbonate, sodium bicarbonate or sodium hydroxide.

Suitable processes are specified, for example, in M. Thiemann et al. in Ullmann's Encyclopedia, 6th Edition, 2000. Electronic Edition, Chapter "Nitric Acid, Nitrous Acid, and Nitrogen Oxides", Section 1.4.2.3.

In general, the $NO_x$ absorption is effected in units in which a gas-liquid phase interface is present, through which mass and heat transfer between the phases is enabled, and which is equipped if required with internal or external equipment for heat supply and/or heat removal. The phases can be conducted in the absorber in cocurrent, in countercurrent or a combination thereof.

According to the invention, the absorption may be carried out in one or more stages.

According to the invention, the absorption is effected at temperatures between −20 and 100° C., preferably between 0 and 60° C., more preferably between 0 and 40° C., and at pressures between 0.1 and 100 bar, preferably between 1 and 30 bar.

Possible embodiments of the absorber are columns having trays, for example bubble-cap trays or sieve trays, columns having structured internals, for example structured packings, columns having unstructured internals, for example random packings, or apparatus in which the liquid phase is present in dispersed form, for example by spraying in nozzles, or a combination thereof.

In a further preferred embodiment, the present invention therefore relates to a process as described above, wherein step B comprises the absorption of nitrogen oxides in acidic or alkaline solution.

In the context of the present invention, $NO_x$ is preferably removed by absorption in an acidic or an alkaline solution. The absorption is carried out between −20 and 120° C., in particular between −10 and 75° C., preferably between 0 and 60° C., for example between 0 and 40° C., and at a pressure between 0.2 and 100 bar, in particular between 0.5 and 50 bar, preferably between 1 and 10 bar.

When the $NO_x$ concentration in the $N_2O$-containing gas mixture is more than 1% by volume, the solvent used for step B is preferably aqueous nitric acid having an $HNO_3$ content between 0 and 69% by weight, preferably between 0 and 10% by weight. It is advantageous in this case that the $NO_x$ depletion in the gas phase is accompanied by the preparation of nitric acid with 1-69% by weight of $HNO_3$. For the purposes of further utility, preference is given to preparing nitric acid having 30-60% by weight of $HNO_3$.

In the context of the present invention, this procedure is used with preference, for example, when the $N_2O$-containing reactant gas stems from a carboxylic acid process (for example adipic acid), wherein $NO_x$ concentrations of from 1 to 50% by volume are present. The $NO_x$ removal in step B is in this case preferably carried out before the $N_2O$ concentration in step A1 and A2.

In one embodiment of the present invention, steps A1 and A2 may be followed by a further step B, preferably a chemical scrubbing, more preferably with sodium carbonate solution or sodium hydroxide solution.

In the context of the present invention, it is possible, for example, to replace the chemical carbonate scrubbing with a selective catalytic reduction with ammonia in which $N_2O$ behaves inertly. This technology, known as SCR-DeNOx or DeNOx technology, is described, for example, in Ullmann's Encyclopedia of Chemical Technology, Chapter "Air", Section 7.2.3.1. "Catalytic Reduction of Nitrogen Oxides in Flue Gases and Process Off-Gases", by J. Wolf et al., 6$^{th}$ edition (Online Edition), 2000. In this preferred embodiment of the present invention, it is possible to attain $NO_x$ concentrations of less than 100 ppm, preferably less than 50 ppm, for example less than 25 ppm, and more preferably of up to 5 ppm, and very low $NH_3$ concentrations in the product, for example less than 10 ppm.

In a particularly preferred embodiment of the present invention, the gas mixture comprising dinitrogen monoxide which is used in the process according to the invention may stem from an adipic acid plant. Preference is given to mixing and cooling the offgas of the adipic acid plant with NO synthesis gas. The gaseous stream is then compressed, preferably to 7 bar, and admixed if appropriate with air. The hot gas is cooled after the compression and passed into an absorption tower in which $NO_x$ is depleted. The gas at the top of the column preferably has a temperature of approx. 40° C. at a pressure of 7 bar.

The offgas may be used directly in the process according to the invention. However, in a more preferred embodiment, the offgas may be heated to from 100 to 250° C., preferably from 150 to 200° C., more preferably to 200° C., and be conducted into the DeNOx plant for the reaction in step B.

Subsequently, the stream is cooled, compressed and cooled again before a single- or multistage absorption/desorption in step A1 and A2 is carried out.

When an $NO_x$ concentration of <1% by volume is present in the $N_2O$-containing gas mixture, for example in the case of an offgas of a nitric acid plant, the absorbent used for step B is preferably an alkaline solution. In the context of the present invention, this procedure is used with preference for the fine purification of the $N_2O$ gas after the concentration in step A1 and A2.

In addition to steps A1, A2 and B, the process according to the invention may also comprise further steps. For example, the process may also comprise a further treatment between the steps A and the step B. Such treatments include, for example, a change in the temperature or a change in the pressure or a change in the temperature and in the pressure.

According to the invention, the gas mixture comprising dinitrogen monoxide which has been purified by the process according to the invention may be used in a further reaction. To this end, the gas mixture may be used in gaseous form. However, it is also possible to initially treat the resulting gas mixture in such a way that the gas mixture is present in liquid or supercritical form and is then used in a further reaction. The gas mixture may be liquefied by suitable selection of the pressure or of the temperature.

The present invention thus also relates to a process, wherein the resulting gas mixture is liquefied.

The gas mixture comprising dinitrogen monoxide which is obtained by the process according to the invention may in principle be used for all applications in which pure dinitrogen monoxide streams are typically used. In particular, the gas mixtures are suitable, for example, for the oxidation of methanol to formaldehyde, as described, for example, in EP-A 0

624 565 or DE-A 196 05 211. The present invention therefore also relates to the use of the gas mixtures comprising dinitrogen monoxide which are obtainable by a process according to the invention as oxidants for methanol.

The process according to the invention affords gas mixtures comprising dinitrogen monoxide which contain a particularly low content of disruptive and inert secondary components. This is especially advantageous for the use of the gas mixture comprising dinitrogen monoxide as an oxidant, since the small fraction of disruptive or inert secondary components results in hardly any side reactions occurring and it thus being possible to obtain particularly pure products.

The present invention therefore also relates to the use of a gas mixture obtainable by a process according to the invention as described above as an oxidant, in particular as an oxidant for olefins.

In principle, the gas mixtures comprising dinitrogen monoxide which are obtainable in accordance with the invention are suitable for oxidizing olefins. Suitable olefins are, for example, open-chain or cyclic olefins having one or more double bonds. Greater preference is given to cyclic olefins having one or more double bonds, for example cyclopentene, cyclohexene, cycloheptene, cyclooctene, cyclodecene, cycloundecene, cyclododecene, 1,4-cyclohexadiene, 1,5-cyclooctadiene, 1,5-cyclododecadiene or 1,5,9-cyclododecatriene.

This enriched and purified $N_2O$-containing gas stream is suitable very particularly for the oxidation of olefins to ketones. For this purpose, it is possible, preferably either to absorb the gaseous $N_2O$ directly into the olefin to be oxidized or another solvent, or the $N_2O$ may first be liquefied before it is reacted with the olefin.

Especially in the case of the use of a liquefied gas mixture comprising dinitrogen monoxide, it is advantageous when the proportion of inert gases in the gas mixture is very low, since the reactor volume is otherwise unnecessarily enlarged.

The present invention therefore also relates to a process for preparing a ketone, at least
comprising the following steps:
A1 Absorption of the gas mixture in an organic solvent
A2 Desorption of the gas mixture from the laden organic solvent
B Adjusting the content of nitrogen oxides $NO_x$ in the gas mixture to at most 0.5% by volume based on the total volume of the gas mixture.
C Contacting the gas mixture with at least one olefin.

For the preferred embodiments of steps A1, A2 and B, the above remarks apply. For the preparation of a ketone too, the sequence of steps A1, A2 on the one hand and B on the other may vary. According to the invention, step B may be performed after steps A1 and A2. However, it is equally possible that step B is performed before steps A1 and A2. However, step C is in every case performed after steps A1, A2 and B.

It is possible in principle to perform step B before steps A1 and A2. However, it is equally possible in the context of the present invention that step B is performed after steps A1 and A2. In a further embodiment, the present invention therefore also relates to a process for preparing a ketone as described above, in which steps A1 and A2 are performed before step B. In an alternative embodiment, the present invention also relates to a process for preparing a ketone, in which step B is performed before steps A1 and A2.

It is equally possible in the context of the present invention that the process comprises a plurality of steps A1 and A2 or a plurality of steps B, in which case step B may be carried out before or after steps A1 and A2.

The reaction in step C may generally be effected according to any process versions in which the olefin and the gas mixture comprising dinitrogen monoxide react with one another. In particular, both continuous reactions and modes of reaction, and batch reactions are possible. According to the invention, the reaction conditions for step C are selected in such a way that a reaction of the at least one olefin with the gas mixture purified in accordance with the invention takes place. Pressure and temperature may be selected appropriately.

The reaction may be carried out in the presence of a suitable solvent. However, it is equally possible in the context of the invention to carry out the reaction in step C without the addition of a solvent.

However, it is also possible in accordance with the invention that the process for preparing a ketone comprises further steps. For instance, the gas mixture comprising dinitrogen monoxide may be treated, for example, before step C and after steps A1, A2 and B. A possible treatment is, for example, a change in pressure and/or temperature of the gas mixture. A further possible treatment is, for example, absorption in a solvent, so that the absorbed gas mixture may be used in step C. The solvent may be any suitable solvent. The solvent is preferably the olefin which is to be oxidized in step C However, it is also possible in the context of the present invention that the gas mixture comprising dinitrogen monoxide is liquefied by suitable selection of the pressure and/or the temperature or is brought into a supercritical state before step C and after steps A1, A2 and B. The liquefied gas mixture comprising dinitrogen monoxide may then be contacted directly with the olefin in step C.

The present invention therefore also relates in a further embodiment to a process for preparing a ketone as described above, wherein the gas mixture used in step C has been liquefied.

In principle, it is possible in step C of the process according to the invention to use all suitable olefins, for example olefins having from 2 to 18 carbon atoms, in particular olefins having from 5 to 12 carbon atoms. Suitable olefins are, for example, open-chain or cyclic olefins having one or more double bonds. Preference is further given to cyclic olefins having one or more double bonds, for example cyclopentene, cyclohexene, cycloheptene, cyclooctene, cyclodecene, cycloundecene, cyclododecene, 1,4-cyclohexadiene, 1,5-cyclooctadiene, 1,5-cyclododecadiene or 1,5,9-cyclododecatriene.

Particular preference is given to using as the olefin cyclopentene, cyclododecene or 1,5,9-cyclododecatriene. The present invention therefore relates in a preferred embodiment to a process for preparing a ketone as described above, wherein the olefin has been selected from the group consisting of cyclopentene, cyclododecene and 1,5,9-cyclododecatriene.

When the present invention relates to the preparation of a ketone comprising the contacting of the gas mixture which has been purified in accordance with the invention and comprises dinitrogen monoxide with cyclopentene, a mixture G(i) comprising cyclopentene is used in step C of the process according to the invention. A mixture comprising cyclopentanone is obtained. Preferred process conditions of this embodiment are described hereinbelow.

In principle, the mixture G(i), in addition to cyclopentene, may comprise any further compounds. Suitable compounds also include those which cannot react with $N_2O$ in the contacting in step C. Preference is given in this context to those compounds which can in principle react with $N_2O$ but are inert toward $N_2O$ under the reaction conditions selected in step C. The term "inert" as used in the context of this embodiment of the present invention refers to compounds which either do not react with $N_2O$ under the reaction conditions selected in step C or, in comparison to the reaction of cyclopentene with $N_2O$, react to such a restricted extent that their reaction product with $N_2O$ in the mixture resulting from step C is present to an extent of at most 15% by weight, preferably to an extent of at most 10% by weight and more preferably to an extent of at most 5% by weight, based in each case on the total weight of the mixture resulting from step C.

Accordingly, the present invention also relates to a process as described above, wherein the mixture G(i), in addition to cyclopentene, comprises at least one compound which is inert toward $N_2O$ in the contacting in step C.

Suitable inert compounds are alkanes, for example hexane, octane, decane, dodecane, cyclopentane or cyclododecane, or alkylbenzenes, for example benzene, toluene, xylenes, ethylbenzene, or ethers, for example methyl tert-butyl ether, tetrahydrofuran, diethyl ether, or esters, for example methyl acetate, ethyl acetate, methyl benzoate, or nitriles, for example acetonitrile, benzonitrile, or alcohols, for example butanol, 2-ethylhexanol, ethanol, or phenols, for example phenol, cresols, or amines, for example aniline, triethylamine, N,N-dimethylaniline, or mixtures of two or more of the compounds mentioned or two or more compounds of the classes mentioned.

Very particular preference is given to those compounds which do not react with $N_2O$ under the reaction conditions selected in step C.

In the context of an embodiment of the process according to the invention which is preferred in this regard, the reactant mixture G(i) used is a mixture which is obtained from cleavage and partial hydrogenation of dicyclopentadiene in the presence of a solvent and comprises cyclopentene, wherein the solvent is selected from the abovementioned inert compounds. Preference is given in this context to the partial hydrogenation of a 2:1 mixture of dicyclopentadiene and toluene. This process is described, (or example, in JP 2000053597 A, which is incorporated fully in this regard by reference into the context of the present application. According to JP 200053597, cyclopentadiene is obtained by thermolysis of dicyclopentadiene in the presence of an aromatic solvent, preferably toluene, the conversion rate being 98%. The resulting gas is passed into a stainless steel reaction tube which is charged with palladium/alumina catalyst The gas is condensed with a cooler at the outlet of the reaction tube.

In a further preferred embodiment of the process according to the invention, the mixture G(i) consists to an extent of at least 99% by weight, based on the total weight of the mixture G(i), of hydrocarbons. In addition to the hydrocarbons, the mixture G(i) may accordingly also contain up to at most 1% by weight of at least one further compound, and compounds including at least one of the abovementioned inert preferred compounds other than hydrocarbons may be present to an extent of at most 1% by weight. It is also possible for other compounds to be present to an extent of at most 1% by weight, with the proviso that they do not disrupt the conversion of cyclopentene in step C.

The term "hydrocarbon mixture" as used in the context of the present invention refers to a mixture of compounds of which each is an unsubstituted hydrocarbon and therefore consists only of the C and H atoms. The hydrocarbon mixtures used in the context of the present invention contain further compounds to an extent of at most 1% by weight, based on the total weight of the particular mixture G(i). The mixture more preferably contains further compounds to an extent of at most 0.5% by weight, more preferably to an extent of at most 0.1% by weight, more preferably to an extent of at most 0.01% by weight and most preferably to an extent of at most 0.001% by weight. Special preference is given to mixtures G(i) which do not contain any further compounds within the measurement precision of the analytical methods used in each case.

In a preferred embodiment, the mixture G(i) is liquid or supercritical under the reaction conditions selected in step C. Among other mixtures, preference is given in this context to mixtures G(i) which are liquid at ambient temperature and ambient pressure. For instance, this includes mixtures of which each compound present is liquid at ambient temperature and ambient pressure. Equally conceivable are mixtures which are liquid at ambient temperature and ambient pressure and comprise at least one compound which is, for example, solid or gaseous at ambient temperature and ambient pressure, but is in liquid form in the mixture G(i) at ambient temperature and ambient pressure.

In the context of a likewise preferred embodiment of the process according to the invention, a mixture G(i) is used which consists to an extent of at least 99% by weight of $C_5$ hydrocarbons and hydrocarbons having more than 5 carbon atoms. In addition to cyclopentene, it is accordingly possible for at least one further $C_5$ hydrocarbon or at least one hydrocarbon having more than 5 carbon atoms or a mixture of at least one further $C_5$ hydrocarbon and at least one hydrocarbon having more than 5 carbon atoms to be present in G(i).

Accordingly, the present invention also describes a process as described above, wherein the mixture G(i) contains at least 99% by weight of $C_5$ hydrocarbons and hydrocarbons naving more than 5 carbon atoms.

Particularly preferred hydrocarbons having more than 5 carbon atoms include the corresponding hydrocarbons already mentioned above in the context of the inert compounds.

As already mentioned above, the reactant mixtures G(i) used are preferably those mixtures as are obtained in industrial processes. In the context of the present invention, preference is given to mixtures which consist to an extent of at least 95% by weight, more preferably to an extent of at least 97% by weight and particularly preferably to an extent of at least 99% by weight of $C_5$, $C_6$ and $C_7$ hydrocarbons.

Accordingly, the present invention also relates to a process as described above, wherein the mixture G(i) contains to an extent of at least 99% by weight $C_5$ and $C_6$ or $C_5$ and $C_7$ or $C_5$ and $C_6$ and $C_7$ hydrocarbons.

In the context of the present invention, the mixture G(i), in addition to cyclopentene, may comprise either at least one further $C_5$ hydrocarbon or at least one $C_6$ hydrocarbon or at least one $C_7$ hydrocarbon or a mixture of at least one further $C_5$ hydrocarbon and at least one $C_6$ hydrocarbon or a mixture of at least one further $C_5$ hydrocarbon and at least one $C_7$ hydrocarbon or a mixture of at least one further $C_5$ hydrocarbon and at least one $C_6$ hydrocarbon and at least one $C_7$ hydrocarbon.

In a preferred embodiment of the process according to the invention, the reactant mixture G(i) used is a hydrocarbon mixture which is obtained from a steamcracker or a refinery and comprises cyclopentene. In this context, preference is given, for example, to $C_5$ cuts from steamcracker plants which comprise substantially only $C_5$ and $C_6$ hydrocarbons. Hydrocarbons having more than 6 carbon atoms are not present in the $C_5$ cuts obtained industrially which comprise, in addition to cyclopentene, for example, 2-butene, isopentane, 1-pentene, 2-methylbutene-1, trans-2-pentene, n-pentane, cis-2-pentene, 2-methylbutene-2, cyclopentane, 2,2-dimethylbutane, 2-methylpentane, 3-methylpentane, n-hexane and benzene. In general, a $C_5$ cut from a steamcracker plant contains cyclopentene in the range from 5 to 60% by weight and preferably in the range from 15 to 50% by weight.

The present invention therefore also describes a process as described above, wherein the mixture G(i) contains to an extent of at least: 99% by weight a mixture of $C_5$ and $C_6$ hydrocarbons.

According to the invention, this mixture of substantially $C_5$ and $C_6$ hydrocarbons which is preferably obtained as a $C_5$ cut from a steamcracker plant car, be used as such. Preference is given to subjecting the mixture of substantially $C_5$ and $C_6$ hydrocarbons before the inventive conversion in step C to a purification in which lower-boiling compounds in comparison to cyclopentene are in turn removed preferentially. While all conceivable methods can be used in this context, preference is given to distillative separation of the mixture.

In the context of the present invention, preference is given to mixtures G(i) which contain to an extent of at most 10% by weight $C_5$ and/or $C_6$ hydrocarbons which have a lower boiling point than cyclopentene. Should at least one $C_4$ hydrocarbon additionally be present in the mixture G(i) to be purified, the distillation used with preference preferably affords mixtures G(i) which contain to an extent of at most 10% by weight $C_4$ and/or $C_5$ and/or $C_6$ hydrocarbons which have a lower boiling point than cyclopentene. In the context of the present invention, particular preference is given to obtaining mixtures G(i) which contain to an extent of at most 5% by weight, more preferably to an extent of at most 3% by weight and particularly preferably to an extent of at most 2% by weight, of $C_5$ and/or $C_6$ hydrocarbons which have a lower boiling point than cyclopentene. Should at least one $C_4$ hydrocarbon additionally be present in the mixture G(i) to be purified, the distillation used with preference preferably affords mixtures G(i) which contain to an extent of at most 5% by weight, more preferably to an extent of at most 3% by weight and most preferably to an extent of at most 2% by weight, $C_4$ and/or $C_5$ and/or $C_6$ hydrocarbons which have a lower boiling point than cyclopentene.

Accordingly, the present invention also describes a process as described above, wherein the mixture G(i) contains at least 99% by weight, based on the total weight of the mixture G(i), of $C_5$ and $C_6$ hydrocarbons, and at most 2% by weight, based on the total weight of the mixture G(i), of hydrocarbons having a lower boiling point in comparison to cyclopentene.

In the context of a likewise preferred embodiment of the process according to the invention, a mixture G(i) is used which consists to an extent of at least 99% by weight of $C_5$ and $C_7$ hydrocarbons. In addition to cyclopentene, at least one further $C_5$ hydrocarbon or at least one $C_7$ hydrocarbon or a mixture of at least one further $C_5$ hydrocarbon and at least one $C_7$ hydrocarbon may accordingly be present in G(i).

Accordingly, the present invention also describes a process as described above, wherein the mixture G(i) contains at least 99% by weight of $C_5$ and $C_7$ hydrocarbons.

A particularly preferred example of a $C_7$ hydrocarbon is toluene.

In the context of an embodiment of the process according to the invention which is preferred in this regard, the reactant mixture G(i) used is a hydrocarbon mixture which is obtained from cleavage and partial hydrogenation of dicyclopentadiene in the presence of toluene as a solvent and comprises cyclopentene. Preference is given in this context to partially hydrogenating a 2:1 mixture of dicyclopentadiene and toluene. This process is de scribed, for example, in JP 2000053597 A, which is fully incorporated in this regard by reference into the context of the present application.

The mixtures obtained in this way generally contain cyclopentene in a range from 25 to 75% by weight, preferably in a range from 35 to 65% by weight and more preferably in a range from 40 to 60% by weight. In addition to cyclopentene. the reaction mixtures comprise mainly cyclopentene and toluene. In general, the mixture obtained from cleavage and partial hydrogenation of a mixture of dicyclopentene and toluene which may be used as a mixture G(i) in the process according to the invention consists to an extent of at least 99% by weight of cyclopentene, toluene and cyclopentane.

The mixture obtained in this preferred embodiment, which consists to an extent of at least 99% by weight of cyclopentene. toluene and cyclopentane, may be used as such.

In a more preferred embodiment, the mixture obtained from the cleavage and partial hydrogenation of a mixture of dicyclopentadiene and toluene is subjected before use as mixture G(i) in the process according to the invention to at least one distillative separation in which a low boiler mixture is obtained which contains cyclopentene generally in the range from 60 to 95% by weight, preferably in the range from 70 to 90% by weight and more preferably in the range from 75 to 85% by weight. This low boiler mixture further comprises toluene generally in the range of at most 20% by weight, preferably of at most 10% by weight and more preferably of at most 5% by weight, and cyclopentane generally in the range of from 5 to 25% by weight, preferably in the range from 7 to 22% by weight and more preferably in the range from 10 to 20% by weight. This low boiler mixture is then used in the process according to the invention as mixture G(i).

Preference is further given to the mixture G(i) used in the process according to the invention containing cyclopentene in a range of from 30 to 90% by weight, more preferably in a range from 40 to 90% by weight, even more preferably in a range from 45 to 90% by weight and especially preferably in a range from 50 to 85% by weight, based in each case on the total weight of the mixture G(i).

In particular, the present invention therefore also relates to the use of a cyclopentene-containing hydrocarbon mixture as a reactant for preparing cyclopentanone, wherein the cyclopentanone-containing hydrocarbon mixture is either the $C_5$ cut of a steamcracker plant or the mixture obtained from the partial hydrogenation of cyclopentadiene and comprising cyclopentene or a mixture of the $C_5$ cut of a steamcracker plant and the mixture obtained from the partial hydrogenation of cyclopentadiene and comprising cyclopentene.

The reaction in step C may generally be effected in any process versions in which cyclopentanone is formed from the mixture G(i) comprising cyclopentene and the gas mixture comprising dinitrogen monoxide. In particular, continuous reaction versions and methods of the reaction as a batch reaction are possible.

In a preferred embodiment, the reaction in step C is effected in batch mode. Preference is given in turn to initially charging the mixture G(i) in a suitable reaction vessel. Since the reaction, as described below, is effected preferably at higher pressures than atmospheric pressure, the reaction vessel used is preferably an autoclave.

The mixture G(i) is initially charged generally at temperatures in the range from 0 to 320° C., preferably in the range from 180 to 300° C. and more preferably in the range from 200 to 290° C. The pressures are generally in the range from 1 to 500 bar, preferably in the range from 10 to 365 bar and more preferably in the range from 25 to 250 bar.

After the mixture G(i) has been initially charged at the abovementioned temperatures and pressures, it is contacted with the inventively purified gas mixture comprising dinitrogen monoxide, and the air present in the reaction vessel may be removed at least partly before the contacting by a suitable measure. Preference is given to flushing the reaction vessel with at least one gas or gas mixture, preference being given to flushing, for example, with nitrogen or another inert gas or a mixture of two or more of these gases. Particular preference is given to using nitrogen as the flushing gas.

The mixture G(i) and the inventively purified mixture comprising $N_2O$ are introduced in amounts at which the molar ratio of cyclopentene to $N_2O$ is generally in the range from 0.05 to 5. preferably in the range from 0.5 to 3 and more preferably in the range from 0.9 to 1.5.

For the contacting of the mixtures G(i) and the inventively purified gas mixture comprising dinitrogen monoxide, the latter is generally Introduced into the reaction vessel at a pressure in the range from 5 to 500 bar, preferably in the range from 10 to 365 bar and more preferably in the range from 25 to 250 bar. The temperatures at which the contacting is effected are adjusted by suitable measures such that the reaction of the cyclopentene present in the mixture G(i) with the $N_2O$ present in the inventively purified gas mixture takes place preferably in liquid or supercritical phase. Accordingly, the temperatures at which the reaction takes place are generally in the range from 150 to 320° C., preferably in the range from 180 to 300° C. and more preferably in the range from 200 to 290° C.

In a particularly preferred embodiment of the process according to the invention, the inventively purified gas mixture is initially introduced into the reaction vessel under the above-specified pressures and the temperature in the reaction vessel is subsequently increased at a rate of generally from 1 to 10° C./min, preferably from 1.5 to 5° C./min and more preferably from 2 to 4° C./min.

When the temperature has been increased to such an extent that the above-specified temperature required for the reaction has been attained, this temperature is maintained generally for a period in the range from 1 to 48 h, preferably in the range from 2 to 30 h and more preferably in the range from 5 to 25 h. It is conceivable not to keep the temperature constant, but rather to vary it suitably within the above-specified limits Accordingly, the present invention also relates to a process as described above, wherein step C comprises at least the following stages (a) to (d);
(a) Introducing the mixture G(i) into a reaction vessel at a temperature in the range from 0 to 320° C. and a pressure in the range from 1 to 500 bar;
(b) contacting the reaction mixture G(i) in the reaction vessel with the inventively purified gas mixture comprising dinitrogen monoxide at a pressure in the range from 5 to 500 bar;
(c) increasing the temperature of the mixture obtained in (b) at a rate in the range from 1 to 10° C./min to a temperature in the range from 150 to 320° C.:
(d) holding the temperature set in (c) for a period in the range from 0.1 to 48 h.

On completion of the reaction of the cyclopentene with $N_2O$ the mixture under pressure in the reaction vessel is cooled. The interior of the reaction vessel is decompressed at the same time as or after the cooling, or both during and after the cooling.

In addition to the above-described reaction in a batch reactor, the process according to the invention may in principle be carried out in any other reactor suitable therefor. Equally possible is a combination of two or more identical or different reactors. One example of a way in which the reaction in step C may be carried out is in at least one bubble column. Preference is given to carrying out the reaction in step C in at least one continuous reactor. For example, the reaction in step C may be carried out in a CSTR (continuous stirred tank reactor) or in a CSTR battery. Preference is further given to at least one of the continuous reactors being a continuous tubular reactor.

Accordingly, the present invention also relates to a process as described above, wherein the mixtures G(i) and the gas mixture which has been purified in accordance with the invention and comprises dinitrogen monoxide are contacted in step C in a continuous tubular reactor.

In a further preferred embodiment, at least one of the continuous tube reactors used in accordance with the invention is a tube bundle reactor.

The mixtures G(i) and the gas mixture which has been purified in accordance with the invention and comprises dinitrogen monoxide may be contacted in the continuous reactors essentially under any suitable reaction conditions which allow cyclopentene to react with $N_2O$ to give cyclopentanone. Special preference is given to selecting the reaction conditions in the at least one continuous reactor in such a way that the reaction in step C proceeds in liquid or supercritical phase. Preference is further given to reaction conditions under which the entire reactor contents are liquid. The term "reactor contents" refers to the mixtures G(i) and the gas mixture purified in accordance with the invention after they have been introduced into the reactor, and the mixture resulting from these mixtures.

Special preference is given to introducing the mixtures G(i) and the gas mixture purified in accordance with the invention into the reactor separately from one another.

However, it is equally possible in the context of the present invention to mix the gas mixture which has been purified in accordance with the invention and comprises dinitrogen monoxide and the mixture G(i) or a portion of the mixture G(i), and to introduce this mixture into the reactor. According to the invention, the gas mixture which has been purified in accordance with the invention and comprises dinitrogen monoxide and the mixture G(i) or a portion of the mixture G(i) are mixed at temperatures at which no reaction takes place. Preference is given to effecting the mixing at a temperature in the range from 80 to 200° C., preferably in the range from 90 to 150° C., in particular in the range from 100 to 120° C.

Accordingly, the present invention also relates to a process as described above, wherein the continuous reactor is filled substantially exclusively with liquid during the reaction in step C.

Very particular preference is given to selecting the reaction conditions in such a way that the mixture in the reactor is homogeneous and monophasic.

The mixture G(i) is generally introduced into the continuous reactor at temperatures in the range from 0 to 320° C., preferably in the range from 180 to 300° C. and more preferably in the range from 200 to 290° C., and the pressures are generally in the range from 1 to 500 bar, preferably in the range from 10 to 365 bar and more preferably in the range from 25 to 300 bar.

The gas mixture which has been purified in accordance with the invention and comprises dinitrogen monoxide is generally introduced into the continuous reactor at temperatures in the range from 0 to 320° C., preferably in the range from 180 to 300° C. and more preferably in the range from 200 to 290° C., and the pressures are generally in the range from 5 to 500 bar, preferably in the range from 10 to 365 bar and more preferably in the range from 25 to 300 bar.

In the continuous reactor, the mixtures G(i) and the mixture which has been purified in accordance with the invention and comprises dinitrogen monoxide are contacted. The mixture G(i) and the gas mixture purified in accordance with the invention are introduced in amounts at which the molar ratio of cyclopentene to N₂O is generally in the range from 0.05 to 10, preferably in the range from 0.5 to 7 and more preferably in the range from 1 to 5.

The cyclopentene present in the gas mixture G(i) is reacted with the N₂O present in the gas mixture which has been purified in accordance with the invention in the at least one continuous reactor at temperatures generally in the range from 150 to 320° C., preferably in the range from 180 to 300° C. and more preferably in the range from 200 to 290° C. The pressures in the continuous reactor are generally in the range from 5 to 500 bar, preferably in the range from 10 to 400 bar and more preferably in the range from 100 to 365 bar.

The residence time the reaction mixture in the continuous reactor is generally in the range from 0.1 to 48 h, preferably in the range from 0.2 to 5 h and more preferably in the range from 0.3 to 2.5 h. It is conceivable to not keep the temperature or the pressure or both in the reactor constant, but rather to vary them suitably within the abovementioned limits.

Accordingly, the present invention also provides a process as described above, wherein step C comprises at least the following stages (aa) to (dd):

(aa) introducing the mixture G(i) into a continuous reactor at a temperature in the range from 0 to 320° C. and a pressure in the range from 1 to 500 bar;

(bb) introducing the gas mixture which has been purified in accordance with the invention and comprises dinitrogen monoxide into the continuous reactor at a temperature in the range from 0 to 320° C. and a pressure in the range from 5 to 500 bar;

(cc) contacting the mixture G(i) with the gas mixture purified in accordance with the invention in the continuous reactor at a temperature in the range from 100 to 320° C. and a pressure in the range from 5 to 500 bar;

(dd) reacting the mixtures G(i) and the gas mixture purified in accordance with the invention over a residence time of the reaction mixture in the continuous reactor in the range from 0.1 to 48 h.

The process according to the invention in the above-described process versions using the mixtures G(i) and the gas mixture purified in accordance with the invention achieves cyclopentene conversions which are generally at least 10%, preferably at least 20% and more preferably at least 50%. The upper limit of the conversions is generally 98%, preferably 99% and more preferably 99.9%.

The cyclopentanone selectivities of the reaction based on cyclopentene are in this context generally in the range from 92 to 99.5%.

Accordingly, the present invention also relates to a process as described above, wherein the cyclopentene used is converted in the range from 10 to 99.9%, based on the total amount of cyclopentene used, with the cyclopentanone selectivity based on cyclopentene in the range from 92 to 99.5%.

The mixture which is obtained in step C and comprises cyclopentanone may further be worked up by any suitable processes to recover the cyclopentanone. These more preferably include distillative processes.

When the present invention relates to the preparation of a ketone comprising the contacting of the gas mixture which has been purified in accordance with the invention and comprises dinitrogen monoxide with cyclododecene, cyclododecene is used in step C of the process according to the invention. A mixture comprising cyclododecanone is obtained. Preferred process conditions of this embodiment are described hereinbelow.

Cyclododecene may preferably be prepared from cyclododecatnene by partial hydrogenation. In the process according to the invention, pure cyclododecene or a mixture comprising cyclododecene may be used. In addition, cyclododecene may be present as the cis-isomer or as the trans-isomer or as a mixture of cis- and trans-isomer.

In the context of the inventive reaction of cyclododecene with the gas mixture which has been purified in accordance with the invention and comprises dinitrogen monoxide, at least one suitable solvent or diluent may be used. These Include cyclododecane or cyclododecanone, although substantially all common solvents and/or diluents are suitable, with the proviso that they have neither a C—C double bond nor a C—C triple bond nor an aldehyde group.

In general, there is no need to add a solvent or diluent in the inventive conversion in step C.

The conversion of the cyclododecene in step C may be carried out continuously or in batchwise mode, and combinations of continuous and batchwise mode are also possible. Preference is given to the continuous reaction.

Reactors include any suitable reactors. For example, the conversion of cyclododecene in step C may be carried out in at least one CSTR (continuous stirred tank reactor) with internal or external heat exchanger, in at least one tubular reactor, in at least one loop reactor or a combination of at least two of these reactors. It is equally possible to configure at least one of these reactors in such a way that it has at least two different zones. Such zones may differ, for example, in reaction conditions, for example the temperature or the pressure, and/or the geometry of the zone, for example the volume or the cross section. Also conceivable is an axial temperature profile which can be realized, for example, by cocurrent cooling and appropriate setting of the amount of coolant.

Particular preference is given to carrying out the oxidation of cyclododecene in at least one tubular reactor.

Accordingly, the present invention also relates to a process as described above, wherein the reaction of the cyclododecene with dinitrogen monoxide is carried out in at least one tubular reactor.

The conversion of the cyclododecene is effected preferably at a temperature in the range from 140 to 350° C., more preferably in the range from 200 to 325° C. and particularly preferably in the range from 225 to 300° C.

Accordingly, the present invention also relates to a process as described above, wherein the conversion in step C is carried out continuously in at least one tubular reactor at a temperature in the range from 140 to 350° C.

The pressure in the reaction vessel, preferably in at least one tubular reactor, is generally at values which are greater than or equal to, preferably greater than, the autogenous pressure of the reactant mixture or the product mixture at the selected reaction temperature or the selected reaction temperatures in the reaction vessel. In general, the reaction pressures are in the range from 1 to 14 000 bar, preferably in the range from autogenous pressure to 3000 bar, more preferably in the range from autogenous pressure to 1000 bar and especially preferably in the range from autogenous pressure to 325 bar.

The residence time of the reactants in the reactor is generally up to 30 h, preferably in the range from 0.1 to 30 h, more preferably in the range from 0.25 to 25 h and especially preferably in the range from 0.3 to 20 h.

The molar ratio of the dinitrogen monoxide: cyclododecene reactants is generally from up to 0.05 to 5, preferably in the range from 0.07 to 2, more preferably in the range from 0.1 to 2 and particularly preferably in the range from 0.1 to 1.

Special preference is given to selecting the reaction conditions in such a way that the conversion of cyclododecene is in the range from 5 to 95%, more preferably in the range from 7 to 80% and especially preferably in the range from 10 to 50%.

The term "conversion" as used above refers to the overall conversion of cyclododecene. When the reactant used is exclusively cis-cyclododecene or exclusively transcyclododecene, the overall conversion corresponds to the conversion of the particular isomer. When the reactant used is a mixture of cis- and trans-isomer containing x mol % of cis-isomer and y mol % of trans-isomer, and the cis-isomer is converted to an extent of m % and the trans-isomer to an extent of n %, the overall conversion is calculated as the sum of mx+ny.

In the case that the reactant used is isomer mixture, preference is given in the context of the present invention to carrying out tho reaction in step C in at least two steps, more preferably in two or three steps and most preferably in two steps.

In a first step, a temperature is selected which is preferably in the range from 140 to 300° C., more preferably in the range from 180 to 290° C. and especially preferably in the range from 225 to 275° C. In this first step, mainly the trans-isomer is oxidized to cyclododecanone. In a second step, a temperature elevated in comparison to the first step is selected which is preferably in the range from 165 to 350° C., more preferably in the range from 225 to 325° C. and especially preferably in the range from 275 to 310° C. In this second step, the cis-isomer is oxidized to cyclododecanone.

Accordingly, the present invention also relates to a process as described above, wherein a mixture comprising cis-cyclododecene and trans-cyclododecene is reacted with dinitrogen monoxide in two stages.

Equally, the present invention also relates to a process as described above, wherein the conversion in the first stage is carried out at a temperature in the range from 140 to 300° C. and the conversion in the second stage at a temperature in the range from 165 to 350° C., the temperature in the first stage being lower than the temperature in the second stage.

As far as the further reaction parameters, for example pressure, residence time or reaction vessels, of the two stages of the abovementioned preferred two-stage process are concerned, reference is made on this subject to the general and preferred embodiments of the above-described one-stage process.

The above-described two-stage process may be realized in any suitable process versions. For example, the two-stage process may be carried out in at least two reactors, in which case the lower temperature is set in at least one reactor and the higher temperature in at least one further reactor. It is equally possible to realize the different temperatures in a single reactor which has at least two zones of different temperature. When one reactor having at least two zones of different temperature is used, the two temperatures may merge continuously or discontinuously into one another. For example, particular preference is given in this context to a tubular reactor having an axial temperature profile which can be realized, for example, as described above.

When at least two different reactors are used in the context of the two-stage process, there may be an intermediate treatment of the reactants between at least two of these reactors. Possible intermediate treatments include, for instance:

heating the reactants:

changing the pressure that the reactants are under. Preference is given in this context, for example, to increasing the pressure via, for example, at least one pump and/or at least one compressor:

metering in at least one reactant. In particular, dintrogen monoxide and/or cyclododecene may be metered in. In the case of the cyclododecene, it may be fresh reactant and/or cyclododecene which is not converted in the second stage and is removed from the product stream by at least one suitable measure and recycled into the process.

removal of formed cyclododecanone by at least one suitable measure, for example and with preference by at least one distillative step.

In a further preferred embodiment of the process according to the invention, in the case that the reactant used as a mixture of cis- and trans-cyclododecene, at least one catalyst is added which is capable of catalyzing the attainment of the equilibrium between cis- and trans-isomer under the reaction conditions which are selected for the conversion of the cyclododecene.

It is in principle possible for this purpose to use all suitable catalysts. Particular preference is given in the process according to the invention to using for this purpose at least one catalyst, as is also used for hydrogenations, for example of olefins or polyenes. Special preference is given in the process according to the invention to using those isomerization catalysts which comprise at least one transition metal, including preferably Ru.

The isomerization catalysts used to set the equilibrium between cis- and trans-isomer may either be homogeneous or heterogeneous catalysts. It is equally possible to use at least one homogeneous and at least one heterogeneous catalyst. The heterogeneous catalysts may be used as a suspension catalyst or as a fixed bed catalyst. It is equally possible to use both at least one heterogeneous suspension catalyst and at least one heterogeneous fixed bed catalyst, if appropriate in addition to at least one homogeneous catalyst. Particular preference is given to using at least one homogeneous catalyst.

While it is possible in principle to use all suitable homogeneous catalysts, preference is given to using those which contain Ru as the active metal. Particular preference is further given to using catalysts as described in U.S. Pat. No. 5,180,870, U.S. Pat. No. 5,321,178, U.S. Pat. No. 5,177,278, U.S. Pat. No. 3,804,914, U.S. Pat. No. 5,210,349 U.S. Pat. No. 5,128,296, U.S. Pat. No. 316.917 and in D. R. Fahey in J. Org. Chem. 38 (1973) p. 80-87, whose disclosure-content on this subject is incorporated fully into the context of the present application. Such catalysts are, for instance. $(TPP)_2(CO)_3Ru$, $[Ru(CO)_4]_3$, $(TPP)_2Ru(CO)_2Cl_2$, $(TPP)_3(CO)RuH_2$, $(TPP)_2(CO)_2RuH_2$, $(TPP)_2(CO)_2RuClH$, or $(TPP)_3(CO)RuCl_2$.

A catalyst used with very particular preference is $(TPP)_2(CO)_2RuCl_2$ or a corresponding Cl-free variant, for example $(TPP)_2(CO)_2RuH_2$, where TPP is triphenylphosphine.

In a further preferred embodiment, the catalyst used is prepared in situ in the process according to the invention. In this preparation in situ, the starting materials are, for example and with preference, the compounds ruthenium chloride, ruthenium acetate, ruthenium acetylacetonate or other Ru compounds.

In general, additionally added to the oxidation, apart from the at least one Ru component, is at least one of the compounds $NR_3$, $PR_3$, $AsR_3$ or $SbR_3$, where R is an alkyl, aralkyl, alkaryl or aryl radical having preferably from 1 to 20 carbon atoms. Special preference is given in the context of the present invention to triphenylphosphine.

In the context of a further embodiment, the oxidation is carried out in the presence of at least one carboxylic acid, as described in DE 198 56 862 A1, whose content on this subject is incorporated fully by reference into the context of the present application.

The carboxylic acid used may, for example, be aliphatic, cycloaliphatic, aromatic or araliphatic carboxylic acids Preference is given to using those which are soluble under the reaction conditions in the reaction system. Preference is given, for instance, to $C_1$-$C_{20}$ monocarboxylic acids, $C_2$-$C_6$ dicarboxylic acids, cyclohexylcarboxylic acid, benzoic acid, terephthalic acid, phthalic acid or phenylacetic acid. Particularly preferred acids are aliphatic mono- and dicarboxylic acids, especially acetic acid, propionic acid and $C_{12}$-$C_{20}$ fatty acids, succinic acid and adipic acid.

In the in situ preparation of the catalyst, particular preference is given to also using at least one CO source. This may be CO itself. Further possible CO sources are, for example, formaldehyde, methanol, ethanol or other suitable primary alcohols, for example benzyl alcohol or diols or polyols having at least one primary alcohol group, for example ethylene glycol, propylene glycol or glycerol.

From the inventive oxidation of cyclododecene, a product mixture generally results. This product mixture preferably contains in the range from 5 to 95% by weight, more preferably from 7 to 80% by weight and especially preferably from 10 to 75% by weight, of cyclododecanone, based in each case on the total weight of the product mixture after cooling to 20° C. and decompression to standard pressure As further constituents, the product mixture comprises any catalyst which has been used before the oxidation stage and not removed, unconverted cyclododecene, and also any compounds introduced into the oxidation with the reactant, for example cyclododecane, and compounds also converted in the reaction with dinitrogen monoxide, as described below.

The isomerization catalyst used for the reaction may subsequently either be recycled into the process, be discarded or be worked up, for example in order to recover the at least one metal present in the catalyst. When the catalyst is recycled into the process, it may be recycled either into the process stage of the reaction with dinitrogen monoxide or into any other step that the process according to the invention may additionally have. In a particularly preferred embodiment described below, the process according to the invention has, as such an additional step, the partial hydrogenation of at least one cyclododecatriene, and the partial hydrogenation mentioned is more preferably effected in the presence of the same catalyst which is used as the isomerization catalyst to set the equilibrium between cis- and trans-isomer of cyclododecene. Accordingly, the removed catalyst may be added to this partial hydrogenation too, in which case the catalyst may be subjected to a suitable regeneration step before it is added.

The cyclododecene used as a reactant, which may be used either as the cis-isomer or as the trans-isomer or as a mixture of cis- and trans-isomer, may in principle stem from any source.

Very particular preference is given in the context of the present invention to preparing cyclododecene by partial hydrogenation of at least one cyclododecatriene, preferably by partial hydrogenation of at least one 1,5,9-cyclododecatriene, for example cis,trans,trans-1,5,9-cyclododecatriene or cis,cis,trans-1,5,9-cyclododecatriene or all-trans-1,5,9-cyclododecatriene and especially from cis,trans,trans-1,5,9-cyclododecatriene.

These preferred compounds may be prepared, for example, by trimerization of pure 1,3-butadiene, as described, for example, in I, Schiffer, G. Oenbrink, "Cyclododecatnene, Cyclooctadiene, and 4-Vinylcyclohexene", Ullmann's Encyclopedia of Industrial Chemistry, 6th Edition (2000), Electronic Release, Wiley VCH. This process forms, for example in the case of trimerization in the presence of Ziegler catalysts, cis,trans,trans-1,5,9-cyclododecatriene., cis,cis,trans-1,5,9-cyclododecatriene and all-trans-1,5,9-cyclododecatriene, as described, for example, in H. Weber et al. "Zur Bildungsweise von cis,trans,trans-Cyclododecatrien-(1.5.9) mittels titanhaltiger Katalysatoren" in: Liebigs Ann. Chem. 681 (1965) p.10-20. While all of these cyclododecatrienes can be partially hydrogenated in the context of the process according to the invention, particular preference is given, as described above, to the conversion of cis,trans,trans-1,5,9-cyclododecatriene in the context of the present process according to the invention. This cis,trans,trans-1,5,9-cyclododecatriene is more preferably prepared according to the abovementioned article of Weber et al., whose content on this subject is incorporated fully into the context of the present application.

Accordingly, the present invention also describes a process as described above, wherein the cyclododecatriene is prepared by trimerization of 1,3-butadiene using a titanium catalyst.

While it is possible in principle to use all suitable titanium catalysts for the trimerization, particular preference is given to the titanium tetrachloride/ethylaluminum sesquichloride catalyst described in the article by Weber et al.

The butadiene used for the trimerization especially preferably has a degree of purity, determined by gas chromatography, of at least 99.6% and more preferably of at least 99.65%. Especially preferably, the 1,3-butadiene used contains no 1,2-butadlene and no 2-butyne within the precision of detection.

From this preferred trimerization, mixtures are generally obtained which contain at least 95% by weight, preferably at least 96% by weight and more preferably at least 97% by weight, of cis,trans,trans-1,5,9-cyclododecatriene. For example, special preference is given to the mixtures containing about 98% by weight of cis,trans,trans-1,5,9-cyclododecatriene.

Therefore, the present invention also relates to a process for preparing cyciododecanone, wherein the cyclododecanone used in step C is prepared by partial hydrogenation of cyclododecatriene.

The cyclododecatriene used in this process is preferably prepared by trimerizing 1,3-butadiene.

The trimerization is effected preferably in the presence of a titanium catalyst; the resulting cyclododecatriene is preferably cis,trans,trans-1,5,9-cyclododecatriene.

The present invention also further describes an integrated process for preparing cyclododecanone which comprises at least the following steps (a) and (b) and also (i) and (ii):

(a) preparation of cyclododecatriene from 1,3-butadiene;
(b) partial hydrogenation of the cyclododecatriene to obtain cyclododecene;
(i) provision of a dinitrogen monoxide-containing gas mixture containing in each case from 0 to 0.5% by volume of oxygen and/or nitrogen oxides, based on at least one offgas stream of an adipic acid plant and/or of a nitric acid plant and/or of a hydroxylamine plant and/or of a nitric acid plant operated with the offgas of an adipic acid plant and/or of a dodecanedioic acid plant and/or of a hydroxylamine plant;
(ii) reaction of cyclodecene obtained in (b) with the gas mixture provided in (i) to obtain cyclododecanone.

Processes for the catalytic partial hydrogenation of cyclododecatriene are described in the literature. It is generally essential that the yield in this reaction is very high, since the small differences in mass and polarity result in the reactants and products being separable from one another by distillation only with a high level of complexity and expense, if at all. The cyclododecatriene conversion therefore has to be substantially quantitative.

The hydrogenation of polyenes to monoenes over homogeneous Ru catalysts with addition of water is described, for example, in U.S. Pat. No. 5,180,870. In example 2 of this document, a cyclododecatriene conversion of 98.4% is attained after a reaction time of 4 h with addition of water. What cyclododecene yield is obtained is not stated. In example 1 of this document, only an unsatisfactory conversion of 85.8% is attained with addition of somewhat less water than in example 2 after a reaction time of 8 h.

U.S. Pat. No. 5,321,176 describes the addition of amines to the homogeneously catalyzed hydrogenation.

In U.S. Pat. No. 5,177,278, the cyclododecatriene hydrogenation is undertaken with homogeneous Ru catalysts in the presence of solvents such as ethers or esters. In the examples of this document, the best cyclododecene selectivities are 96-98%. However, quantitative conversion is never achieved, so that a separation problem presents Itself in the workup.

In U.S. Pat. No. 3,925,494, operation is likewise effected in solvents. The maximum cyclododecene yield is stated to be approx. 95%. However, the conversion is not quantitative here either.

In J. Org. Chem. 38 (1973) p 80-87, D. R Fahey describes the hydrogenation of cyclododecatriene over various homogeneous Ru catalysts. In all the examples, operation is effected in the presence of relatively large amounts of solvent. Cyclododecene yields of approx. 98% are described. However, the stated amount of Ru used, based on cyclododecatriene, is very high.

DE 198 56 862 A1 describes the hydrogenation of cyclododecatriene over homogeneous Ru catalysts in the presence of carboxylic acids. Cyclododecene yields of 98% can be achieved in this case.

In the context of the present invention, the catalytic partial hydrogenation of cyclododecatriene to cyclododecene may be effected by all suitable methods.

In particular, the catalytic partial hydrogenation may be carried out with homogeneous or heterogeneous catalysts, and the heterogeneous catalysts may be used in the form of a suspension or in the form of a fixed bed.

The heterogeneous catalyst systems used are preferably those which contain at least one of the elements Pd, Pt, Ru, Ir, Ni and Rh as the active hydrogenating metal.

In a particularly preferred embodiment, cyclododecatriene is partially hydrogenated to cyclododecene in the process according to the invention in the presence of at least one homogeneous hydrogenation catalyst.

While it is possible in principle to use all suitable homogeneous catalysts, preference is given to using those which contain Ru as the active hydrogenating metal. Particular preference is further given to using catalysts as described in U.S. Pat. No. 5,180,870, U.S. Pat. No. 5,321,176, U.S. Pat. No. 5,177,278, U.S. Pat. No. 3,804,914, U.S. Pat. No. 5,210,349, U.S. Pat. No. 5,128.296, U.S. Pat. No. 316,917 and in D.R. Fahey in J. Org. Chem. 38(1973) p. 80-87, whose disclosure-content on this subject is incorporated fully into the context of the present application. Such catalysts are, for instance, $(TPP)_2(CO)_3Ru$, $[Ru(CO)_4]_3$, $(TPP)_2Ru(CO)_2Cl_2$, $(TPP)_3(CO)RuH_2$, $(TPP)_2(CO)_2RuH_2$, $(TPP)_2(CO)_2RuClH$ or $(TPP)_3(CO)RuCl_2$.

A catalyst used with very particular preference is $(TPP)_2(CO)_2RuCl_2$ or a corresponding Cl-free variant, for example $(TPP)_2(CO)_2RuH_2$, where TPP is triphenylphosphine.

In a further preferred embodiment, the catalyst used for partial hydrogenation is prepared in situ in the process according to the invention. In this, preparation the starting materials are, for example and with preference, the compounds ruthenium chloride, ruthenium acetate, ruthenium acetylacetonate or other Ru compounds.

In general, additionally added to the hydrogenation reaction, apart from the at least one Ru component, is at least one of the compounds $NR_3$, $PR_3$, $AsR_3$ or $SbR_3$ where R is an alkyl, aralkyl, alkaryl or aryl radical having preferably from 1 to 20 carbon atoms. Special preference is given in the context of the present invention to triphenylphosphine.

Based on 1 kg of cyclododecatriene, calculated as the metal, generally from 0.1 to 2000 mg of active hydrogenating metal, more preferably Ru, are used in the process according to the invention. Preference is given to using from 1 to 1000 mg and particular preference to using from 10 to 200 mg.

In one embodiment of the process according to the invention, the catalyst is removed from the reactants on completion of partial hydrogenation. In a further embodiment of the present invention, the catalyst removed is fed to any process and very particular preference is given to recycling it into the process according to the invention. According to the invention, the catalyst is more preferably removed in at least one distillation, in which case the product of the partial hydrogenation, cyclododecene, is removed via the top, and the catalyst, in some cases with fractions of cyclododecene, via the bottom.

As a consequence of the very small amounts of catalyst material as described above and therefore the very low costs for the catalyst, it is generally not necessary in the process according to the invention to remove the catalyst from the reaction mixture after the partial hydrogenation and recycle it into the process.

In a further embodiment, the partial hydrogenation is carried out in the presence of at least one carboxylic acid, as described in DE 198 56 862 A1, whose contents on this subject are fully incorporated by reference into the context of the present application.

The carboxylic acid used may be, for example, an aliphatic, cycloaliphatic, aromatic or araliphatic carboxylic acid. Preference is given to using those which are soluble in the reaction system under the reaction conditions. Examples are $C_1$-$C_{20}$ monocarboxylic acids, $C_2$-$C_6$ dicarboxylic acids, cyclohexanecarboxylic acid, benzoic acid, terephthalic acid, phthalic acid or phenylacetic acid. Particularly preferred acids are aliphatic mono- and dicarboxylic acids, in particular acetic acid, propionic acid and $C_{12}$-$C_{20}$ fatty acids, succinic acid and adipic acid.

The amount of acid added per kg of cyclododecatriene is generally from 0.001 to 100 g, preferably from 0.01 to 50 g and more preferably from 0.05 to 25 g.

In the in situ preparation of the catalyst, particular preference is given to also using at least one CO source. This may be CO itself. Further possible CO sources are, for example, formaldehyde, methanol, ethanol or other suitable primary alcohols, for example benzyl alcohol or diols or polyols having at least one primary alcohol group, for example ethylene glycol, propylene glycol or glycerol.

In the process according to the invention, the partial hydrogenation generally takes place at temperatures in the range from 50 to 300° C., preferably in the range from 80 to 250° C. and more preferably in the range from 100 to 200° C. The reaction pressures are in the range from 1 to 300 bar, preferably in the range from 1 to 200 bar and more preferably in the range from 1 to 100 bar.

The reaction times per batch in batch mode, or the residence times in the case of the continuous process version, are generally in the range from 0.5 to 48 h. They are determined substantially by the batch sizes and the possibilities of being able to supply and remove energy. The above-described carboxylic acid addition makes it uncritical if the reaction batch is handled under reaction conditions for longer than necessary. This makes possible considerably simplified reaction control and reaction monitoring.

The preferred process version of the partial hydrogenation is the continuous mode. Examples of preferred reactors are stirred reactors or reactors mixed by pumps, in which the introduction of hydrogen should be very efficient. This may be achieved, for example, by baffles in stirred systems or in other systems.

In one of the preferred embodiments of the present invention, at the location where the hydrogenation takes place the heat released is removed and used, for example, to raise steam. This process version is for example, preferably carried out in at least one tube bundle reactor. When tubular reactor systems are used, it is advantageous, for example by suitable internals, to accelerate the mixing-in of hydrogen, as is customary, for example, in packed bubble columns.

To complete the conversion, it is possible in the context of the present invention to operate at least two reactors in series. For example, a first reactor may have vigorous mixing, which may be achieved, for example, by product recycling by means of a pump, while a second and optionally a third reactor are merely flowed through, and hydrogen may optionally be added. In a preferred embodiment of the specific process version, a conversion in the range from 80 to 98% is achieved in the first reactor, while the postreactor or postreactors ensure the remaining conversion.

When starting up the hydrogenation, special preference is given to not initially charging the cyclododecatriene reactant, or to not initially charging it pure together with catalyst and/or catalyst precursor, since this may result in undesired exothermic reactions. In general, at least one suitable solvent or diluent may be added. Useful such solvents or diluents are for instance, cyclododecane, cyclododecene, saturated aliphatic hydrocarbons, aromatic hydrocarbons or mixtures of two or more thereof. In a preferred embodiment, cyclododecene or cyclododecane or a mixture of cyclododecene and cyclododecane or a mixture of cyclododecene and cyclododecatriene or a mixture of cyclododecane and cyclododecatriene or a mixture of cyclododecene, cyclododecane and cyclododecatriene is initially charged. While the cyclododecatriene content of the corresponding mixtures is generally uncritical, in the continuous process it is preferably in the range of up to 30% by weight, more preferably up to 25% by weight and especially preferably up to 20% by weight.

Accordingly, the present invention also relates to a process as described above, wherein the partial hydrogenation is started up by initially charging a mixture of cyclododecane and/or cyclododecene together with cyclododecatriene, the cyclododecatriene content of this mixture being in the range of up to 30% by weight.

The product which is obtained from the inventive partial hydrogenation is generally a mixture. In a preferred embodiment, this mixture contains cyclododecene in a range from 92 to 99.9% by weight, more preferably in a range from 94 to 99% by weight and especially preferably in the range from 96 to 98% by weight, based in each case on the total weight of the product mixture.

In general, cyclododecene is obtained as a mixture of cis- and trans-isomer. In general, the molar ratio of cis-isomer to trans-isomer is in the range from 0.4:1 to 2.0:1.

In addition to cyclododecene, the product mixture generally contains cyclododecane in a range from 0.1 to 8% by weight, preferably in a range from 0.3 to 7% by weight and more preferably in the range from 0.5 to 6.5% by weight, based in each case on the total weight of the product mixture.

In addition to cyclododecene and cyclododecane, the product mixture may contain traces of cyclododecadiene and/or unconverted cyclododecatriene and/or catalyst. The process according to the invention may in principle be conducted in such a way that the cyclododecatriene used is converted fully to cyclododecene. In general, the product mixture contains the unconverted cyclododecatriene reactant in an amount of less than 0.5% by weight, preferably of less than 0.25% by weight and especially preferably of less than 0.1% by weight, based in each case on the total weight of the product mixture.

If desired, unconverted cyclododecatriene may be removed from the product mixture by at least one suitable method, for example and with preference at least one distillative measure, and recycled into the process. As a consequence of the very high conversion of cyclododecatriene, particular preference is given in the process according to the invention to not removing it from the product mixture from the partial hydrogenation and to feeding traces of cyclododecatriene together with the cyclododecene to the oxidation with dinitrogen monoxide in step C.

In a preferred embodiment of the process according to the invention, the at least one catalyst used for the partial hydrogenation may be removed from the product mixture of the partial hydrogenation. This removal may be effected by any suitable process depending on the catalyst used.

When the catalyst used in the partial hydrogenation is, for example, a heterogeneous catalyst as a suspension catalyst, preference is given in the context of the present invention to removing it by at least one filtration step. The catalyst removed in this way may subsequently either be recycled into the process or be used in another process, discarded or worked up, for example in order to recover the at least one metal present in the catalyst.

When the catalyst used in the partial hydrogenation is, for example, a homogeneous catalyst, preference is given in the context of the present invention to removing it by at least one distillation step. In this distillation, one or two or more distillation columns may be used.

In the at least one distillation column, the product mixture from the partial hydrogenation is separated into at least 2 fractions. The high boiler fraction comprises substantially the entire amount of the homogeneous hydrogenation catalyst used. The catalyst removed in this way may, optionally after at least one suitable regeneration step, subsequently either be recycled into the process, discarded or worked up, for example in order to recover at least one metal present in the catalyst. It is also possible to use the removed catalyst in another process.

In a particularly preferred embodiment of the process according to the invention, a portion of the homogeneous hydrogenation catalyst removed in this way may be recycled into the process and the remainder of the catalyst removed discharged from the process.

The main fraction from the abovementioned distillative workup of the product mixture from the partial hydrogenation comprises substantially cyclododecene, with small traces of cyclododecane and in some cases traces of cyclododecadienes, as has already been described above.

In a preferred embodiment of the process according to the invention, this main fraction is fed to the oxidation with dinitrogen monoxide in step C.

It is equally possible to remove low boilers from the main fraction in at least one suitable
distillation step before feeding to the oxidation.

In a further preferred embodiment of the process according to the invention, the at least one catalyst used for the partial hydrogenation is not removed from the product mixture of the partial hydrogenation. Particular preference is given to this embodiment when a homogeneous catalyst is used for the hydrogenation. Preference is further given in this case to not working up the product mixture from the partial hydrogenation and feeding it directly to the oxidation with dinitrogen monoxide in step C.

As already described above, in a preferred embodiment of the oxidation of cyclododecene with dinitrogen monoxide in step C, a suitable catalyst is used which is capable of catalyzing the establishment of equilibrium between cis- and trans-isomer of cyclododecene.

In a particularly preferred embodiment, the catalyst used for this establishment of equilibrium is the same catalyst as for the partial hydrogenation of cyclododecatriene.

Accordingly, the present invention also relates to a process as described above, wherein the hydrogenation of cyclododecatriene to cyclododecene and the conversion of cyclododecene to cyclododecanone with dinitrogen monoxide in step C are effected in the presence of the same catalyst.

A considerable process technology advantage of the process according to the invention is the fact that when the same homogeneous catalyst is used in partial hydrogenation and oxidation with dinitrogen monoxide, the catalyst does not have to be removed from the product mixture of the partial hydrogenation, and that this mixture may be fed directly to the oxidation with dinitrogen monoxide without costly and inconvenient distillative workup of the catalyst.

Accordingly, the present invention also relates to a process as described above, wherein a mixture resulting from the hydrogenation of cyclododecatriene to cyclododecene in the presence of a homogeneous catalyst, comprising cyclododecene and homogeneous catalyst, may be used as a reactant for the reaction with dinitrogen monoxide.

In the context of the present invention, it is also possible to remove only a portion of the catalyst from the product mixture of the partial hydrogenation and to feed the resulting mixture, comprising cyclododecene and the remaining portion of the catalyst, to the oxidation with dinitrogen monoxide. In this case, at least one further catalyst may optionally be added in the oxidation with dinitrogen monoxide. It is also possible not to remove the catalyst from the product mixture of the partial hydrogenation and to add the same and/or at least one further catalyst in the oxidation with dinitrogen monoxide.

One of the advantages of the above-described process according to the invention for preparing cyclododecanone is that cyclododecanone is obtained in few steps and simultaneously with high selectivity. A further considerable advantage is the fact that the reactant used for the process according to the invention may be dinitrogen monoxide-containing offgases from preferably industrial plants, which firstly are available without great cost and inconvenience and secondly enable the integration of the process according to the invention into an existing integrated plant system, which allows the transport path for the reactant to be kept to a minimum, and said offgases also, as potential greenhouse gases, do not have to be fed to a special treatment for disposal, but rather flow directly into a product of value.

The cyclododecanone prepared in accordance with the invention may, for example and with particular preference, be used to prepare dodecanedicarboxylic acid and/or laurolactam and/or polymers derived therefrom, for example polyamides such as nylon-12 or nylon-6,12.

When the present invention relates to the preparation of a ketone comprising the contacting of the gas mixture which has been purified in accordance with the invention and comprises dinitrogen monoxide with cyclododecatriene, cyclododecatriene is used in step C of the process according to the invention. A mixture comprising cyclododecadiene is obtained. Preferred process conditions of this embodiment are described hereinbelow.

The resulting cyclododecadiene may preferably be converted to cyclododecanone by hydrogenation.

The preparation of cyclododeca-4,8-dienone from 1,5,9-cyclododecatriene had hitherto been possible only via a two-stage synthesis in which 1,5,9-cyclododecatriene was epoxidized in a first step to 1,2-epoxycyclododeca-5,9-diene and the epoxide was rearranged catalytically to cyclododeca-4,8-dienone in a second step. This process is described, for example, in U.S. Pat. No. 3,063,986. This conventional process has two decisive disadvantages: firstly, it is difficult to achieve a selective monoepoxidation. Secondly, the process necessarily has two stages.

Accordingly, the above-described embodiment preferred in the context of the process according to the invention offers the possibility of obtaining cyclododeca-4,8-dienone starting from 1,5,9-cyclododecatriene in a single step at high selectivity.

The overall process according to the invention for preparing cyclododecanone accordingly comprises steps A1, A2, B and C, in which case cyclododecatriene is reacted with dinitrogen monoxide in step C to obtain cyclododecadienone and, in a further step, the cyclododecadienone is hydrogenated to obtain cyclododecanone.

Compared to the above-described common process which necessarily comprises the four steps of:

full hydrogenation of cyclododecatriene to cyclododecane:
air oxidation of the cyclododecane in the presence of boric acid to give cyclododecyl borate;
hydrolysis of the borate to give cyclododecanol;
dehydrogenation of the cyclododecanol to obtain cyclododecanone, the process according to the invention for preparing cyclododecanone is accordingly notable, among other features, in that the cyclododecanone product can be prepared starting from the same reactant, cyclododecatriene, with a saving of two reaction stages, and the number of reaction stages can thus be halved.

In the context of the inventive reaction of cyclododecatriene with dinitrogen monoxide in step C, it is possible to use at least one suitable solvent or diluent. Substances suitable as such include cyclododecane or cyclododecanone or saturated aliphatic or aromatic, optionally alkyl-substituted hydrocarbons, although substantially all common solvents and/or diluents are suitable, with the proviso that they have neither a C—C double bond nor a C—C triple bond nor an aldehyde group.

In general, there is no need to add a solvent or diluent in the inventive reaction with dinitrogen monoxide in step C.

Generally, there exist no particular restrictions with regard to the reaction conditions of the conversion of cyclododecatriene in step C, as long as it is ensured that cyclododeca-4,8-dienone is obtained from the reaction.

The temperatures in the reaction of cyclododecatriene with dinitrogen monoxide are preferably in the range from 140 to 350° C., more preferably in the range from 180 to 320° C. and particularly preferably in the range from 200 to 300° C.

In the context of the process according to the invention, it is possible to carry out the reaction in step C at two or more temperatures or in two or more temperature ranges, each of which is within the above-specified limits. Temperature changes in the course of the reaction may be undertaken continuously or else discontinuously.

The pressures in the reaction of cyclododecatriene with dinitrogen monoxide in step C are preferably higher than the autogenous pressure of the reactant mixture or product mixture at the selected reaction temperature or the selected reaction temperatures. The pressures are preferably in the range from 1 to 1000 bar, more preferably in the range from 40 to 300 bar and particularly preferably in the range from 50 to 200 bar.

In the context of the process according to the invention, it is possible to carry out the reaction at two or more pressures or within two or more pressure ranges, each of which is within the above-specified limits. Pressure changes in the course of the reaction may be undertaken continuously or else discontinuously.

Accordingly, the present invention also relates to a process as described above, wherein the reaction in step C is carried out at a temperature in the range from 140 to 350° C. and a pressure in the range from 1 to 1000 bar.

With regard to the reactors which can be used for the conversion in step C, there exist no particular restrictions. In particular, the conversion may be effected in batch mode or in continuous mode. Accordingly, the reactors used may, for example, be at least one CSTR (continuous stirred tank reactor) having at least one internal and/or at least one external heat exchanger, at least one tubular reactor or at least one loop reactor. It is equally possible to configure at least one of these reactors in such a way that it has at least two different zones. Such zones may differ, for example, in reaction conditions, for example the temperature or the pressure, and/or in the geometry of the zone, for example the volume or the cross section. When the conversion is carried out in two or more reactors, two or more identical reactor types or at least two different reactor types may be used.

In a preferred embodiment, the inventive reaction with dinitrogen monoxide in step C is carried out in a single reactor. For example and with preference, the reaction is in continuous mode.

The residence time of the reactants in the at least one reactor is generally in the range of up to 20 h, preferably in the range from 0.1 to 20 hours, more preferably in the range from 0.2 to 15 hours and particularly preferably in the range from 0.25 to 10 h.

In the feed which is fed to the reaction of dinitrogen monoxide with cyclododecatriene in step C, the molar ratio of dinitrogen monoxide to cyclododecatriene is generally in the range from 0.05 to 4, preferably in the range from 0.06 to 1, more preferably in the range from 0.07 to 0.5 and particularly preferably in the range from 0.1 to 0.4.

In a particularly preferred embodiment, the process according to the invention is carried out in such a way that a conversion of cyclododecatriene in the range of up to 50%, preferably in the range from 5 to 30% and especially preferably in the range from 10 to 20% is achieved at a very high selectivity for cyclododecadienone. The selectivity based on cyclododecadienone is generally at least 90%, preferably at least 92.5% and more preferably at least 95%.

Accordingly, the present invention also relates to a process as described above, wherein the reaction of dinitrogen monoxide with cyclododecatriene in step C has a conversion of cyclododecatriene in the range from 1 to 80%, preferably in the range from 5 to 30%, at a selectivity based on cyclododecadienone of at least 90%.

In the context of the present invention, it is possible in principle to convert in step C any cyclododecatriene or any mixture of two and more different cyclododecatrienes with the mixture which has been purified in accordance with the invention and comprises dinitrogen monoxide These include, for example, 1,5,9-cyclododecatrienes, for example cis,trans,trans-1,5,9-cyclododecatriene or cis,cis,trans-1,5,9-cyclododecatriene or all-trans-1,5,9-cyclododecatriene.

In a very particularly preferred embodiment of the process according to the invention, the cyclododecatriene used is cis,trans,trans-1,5,9-cyclododecatriene.

Accordingly, the present invention also relates to a process as described above, wherein the cyclododecatriene used is cis,trans,trans-1,5,9-cyclododecatriene.

In particular, the present invention therefore also describes a process as described above, wherein cis,trans,trans-1,5,9-cyclododecatriene is reacted with dinitrogen monoxide in step C to obtain cyclododeca-4,8-dienone.

In general, a cyclododeca 4,8-dienone isomer mixture results from the inventive reaction of cis,trans,trans-1,5,9-cyclododecatriene with dinitrogen monoxide in step C and comprises at least two of the isomers cis,trans-cyclododeca-4,8-dienone, trans,cis-cyclododeca-4,8-dienone and trans,trans-cyclododeca-4,8-dienone. Preference is given in accordance with the invention to obtaining an isomer mixture in which trans,cis-isomer and cis,trans-isomer are obtained in about the same amounts and the trans,trans-isomer is formed in only small amounts in comparison to the two other isomers. An example of a typical isomer mixture accordingly has the isomers in molar ratios of about 1:1:0.08.

The inventive conversion of at least one cyclododecatriene, preferably the conversion of at least one 1,5,9-cyclododecatriene and especially preferably the conversion of cis,trans,trans-1,5,9-cyclododecatriene in step C may in principle be effected in the presence of a catalyst. In a particularly preferred embodiment of the process according to the invention, the reaction with dinitrogen monoxide in step C is carried out without addition of a catalyst.

Accordingly, the present Invention also describes a process as described above, wherein the reaction of cyclododecatriene with dinitrogen monoxide in step C is carried out without addition of a catalyst.

In general, there is no need to add a solvent or diluent in the inventive reaction in step C with dinitrogen monoxide.

The 1,5,9-cyclododecatriene used with preference may be prepared, for example, by trimerization of pure 1,3-butadiene, as described, for example, in T. Schiffer, G. Oenbrink, "Cyclodecatriene, Cyclooctadiene, and 4-Vinylcyclohexene", Ullmann's Encyclopedia of Industrial Chemistry, 6th Edition (2000), Electronic Release, Wiley VCH. This process forms, for example in the case of trimerization in the presence of Ziegler catalysts, cis,trans,trans-1,5,9-cyclododecatriene, cis,cis,trans-1,5,9-cyclododecatriene and all-trans-1,5,9-cyclododecatriene, as described, for example, in H. Weber et al. "Zur Bildungsweise von cis,trans,trans-Cyclododecatrien-(1.5.9) mittels titanhaltiger Katalysatoren" in: Liebigs Ann. Chem. 681 (1965) p. 10-20. While all of the cyclododecatrienes can be oxidized individually or as a mixture of two or more thereof by means of dinitrogen monoxide in the process according to the invention, particular preference is given, as described above, to the conversion of cis,trans,trans-1,5,9-cyclododecatriene in the present process according to the invention. This cis,trans,trans-1,5,9-cyclododecatriene is more preferably prepared in accordance with the abovementioned article of Weber et al., whose content on this subject is incorporated fully by reference into the context of the present application.

Accordingly, the present invention also describes a process as described above, wherein the cyclododecatriene used as a reactant is prepared by trimerization of 1,3-Dutadiene using a titanium catalyst.

While it is possible in principle to use all suitable titanium catalysts for the trimerization, particular preference is given to the titanium tetrachloride, ethylaluminum sesquichloride catalyst described in the article of Weber et al.

The butadiene used for the trimerization especially preferably has a degree of purity, determined by gas chromatography, of at least 99,8% and more preferably of at least 99.65%.

Especially preferably, the 1,3-butadiene contains no 1,2-butadiene and no 2-butyne within the precision of detection.

From this preferred trimerization, mixtures are generally obtained which contain at least 95% by weight, preferably at least 98% by weight and more preferably at least 97% by weight, of cis,trans,trans-1,5,9-cyclododecatriene. For example and with special preference, the mixtures contain about 98% by weight of cis,trans,trans-1,5,9-cyclododecatriene.

This cis,trans,trans-1,5,9-cyclododecatriene-containing mixture may be used as such for the reaction with dinitrogen monoxide in step C. It is equally possible to remove the cis,trans,trans-1,5,9-cyclododecatriene from the mixture by at least one suitable method, for example and with preference by at least one distillation, and to use it in the reaction with dinitrogen monoxide. Preference is given to such a purification not taking place in the process according to the invention.

With regard to further details on the trimerization, reference is made to the article by Weber et al.

From the inventive reaction of cyclododecatriene with dinitrogen monoxide in step c, a mixture is generally obtained which comprises cyclododecadienone, preferably cyclododeca-4,8-dienone, with or without unconverted reactant and with or without at least one by-product. Depending on the further utilization and/or workup, the cyclododecadienone, preferably the cyclododeca-4,8-dienone, may be removed from this mixture. In the case that the mixture comprises cyclododecadienone and, for example, a diketone such as cyclododecenedione, it is possible to remove the cyclododecadienone, preferably the cyclododeca-4,8-dienone, in a simple manner and to feed it to a further process step for example the partial hydrogenation to cyclododecencne or preferably to the hydrogenation to cyclododecenone.

From this mixture, the cyclododeca-4,8-dienone may be removed by at least one suitable method. Preference is given in this context to distillative removal. The distillation is effected at a pressure in the range of generally from 0.001 to 2 bar, preferably in the range from 0.01 to 1 bar and especially preferably in the range from 0.03 to 0.5 bar.

The cyclododecadienone obtained in accordance with the invention from the reaction of cyclododecatriene with dinitrogen monoxide may be fed to one or more arbitrary further processes. For example, the keto group of cyclododecadienone may be subjected to a chemical reaction. Equally, at least one of the C—C double bond may be subjected to a chemical reaction. For example and with preference, at least one C—C double bond, preferably both C—C double bonds, may be hydrogenated.

Irrespective of which regioisomers of cyclododecadiene or which mixture of at least two regioisomeric cyclododecadienones is obtained from the inventive reaction with dinitrogen monoxide, this regioisomer or this regioisomer mixture is preferably hydrogenated to cyclododecanone.

In a particularly preferred embodiment of the process according to the invention, cyclododeca-4,8-dienone is hydrogenated to cyclododecanone.

Accordingly, the present invention also relates to a process as described above, wherein the cyclododecadiene obtained from the reaction of cyclododecatriene with dinitrogen monoxide in step C is hydrogenated to obtain cyclododecanone.

For the hydrogenation of the cyclododecadiene and especially preferably cyclododeca-4,8-dienone, it is possible to use any suitable catalysts. In particular, it is possible to use at least one homogeneous or at least one heterogeneous or both at least one homogeneous and at least one heterogeneous catalyst.

The usable catalysts preferably contain at least one metal from transition group 7, 8, 9, 10 or 11 of the Periodic Table of the Elements. Preference is further given to the catalysts usable in accordance with the invention containing at least one element selected from the group consisting of Re, Fe, Ru, Co, Rh, Ir, Ni, Pd, Pt, Cu and Au. Special preference is given to the catalysts usable in accordance with the invention containing at least one element selected from the group consisting of Fe, Ni, Pd, Pt and Cu. Particular preference is given to the catalysts usable in accordance with the invention containing Pd.

Homogeneous catalysts used with preference in the process according to the invention contain at least one element of transition group 8, 9 or 10. Preference is further given to homogeneous catalysts which contain Ru, Rh, Ir and/or Ni. Examples which should be mentioned in this context are $RhCl(TTP)_3$ or $Ru_4H_4(CO)_{12}$. Particular preference is given to those homogeneous catalysts which contain Ru. For example, homogeneous catalysts used are those described in U.S. Pat. No. 5,180,870, U.S. Pat. No. 5,321,176, U.S. Pat. No. 5,177,278, U.S. Pat. No. 3.804,914, U.S. Pat. No. 5,210, 349 U.S. Pat. No. 5,128,296, U.S. Pat. No. 316,917 and in D.R. Fahey in J. Org. Chem. 38 (1973) p. 80-87, whose disclosure content on this subject is incorporated fully into the context of the present application. Such catalysts are, for instance, $(TPP)_2(CO)_3Ru$, $[Ru(CO)_4]_3$, $(TPP)_2Ru(CO)_2Cl_2$, $(TPP)_3(CO)RuH_2$, $(TPP)_2(CO)_2RuH_2$, $(TPP)_2(CO)_2RuClH$ or $(TPP)_3(CO)RuCl_2$.

Special preference is given in the context of the process according to the invention to using at least one heterogeneous catalyst, in which case it is possible to use at least one of the abovementioned metals in the form of the metal as such, in the form of Raney catalyst and/or applied to a customary support. Preferred support materials are, for instance, activated carbons or oxides, for example aluminas, silicas, titanias or zirconias. Other support materials which should be mentioned include bentonites. When two or more metals are used, they may be present separately or as an alloy. It is possible in this case to use at least one metal as such and at least one metal in the form of Raney catalyst, or at least one metal as such and at least one other metal applied to at least one support, or at least one metal in the form of Raney catalyst and at least one metal applied to at least one support, or at least one metal as such and at least one other metal in the form of Raney catalyst and at least one other metal applied to at least one support.

The catalysts used in the process according to the invention may, for example, also be what are known as precipitation catalysts. Such catalysts may be prepared by precipitating their catalytically active components from their salt solutions, in particular from the solutions of their nitrates and/or acetates, for example by adding solutions of alkali metal hydroxide and/or carbonate and/or alkaline earth metal hydroxide and/or carbonate solutions, for example sparingly soluble hydroxides, oxide hydrates, basic salts or carbonates, subsequently drying the resulting precipitates and then converting them by calcination at generally from 300 to 700° C., in particular from 400 to 800° C., to the corresponding oxides, mixed oxides and/or mixed-valence oxides, which are reduced by a treatment with hydrogen or with hydrogen-containing gases in the range of generally 50-700° C., in particular from 100 to 400° C., to the metals and/or low-oxidation state oxidic compounds in question and converted to the actual catalytically active form. Reduction is generally effected until no more water is formed, in the preparation of precipitation catalysts which comprise a support material, the catalytically active components can be precipitated in the presence of the support material in question. The catalytically active components may advantageously be precipitated from the salt solutions in question simultaneously with the support material.

Preference is given to using hydrogenation catalysts in the process according to the invention which contain the metals or metal compounds catalyzing the hydrogenation deposited on a support material.

Apart from the abovementioned precipitation catalysts which, apart from the catalytically active components, also additionally comprise a support material, support materials suitable for the process according to the invention are generally those in which the catalytically hydrogenating component has been applied to a support material, for example, by impregnation.

The way in which the catalytically active metal is applied to the support is generally not critical and can be brought about in various different ways. The catalytically active metals may be applied to the support materials, for example, by impregnation with solutions or suspensions of the salts or oxides of the elements in question, drying and subsequent reduction of the metal compounds to the metals or low-oxidation state compounds in question by means of a reducing agent, preferably with hydrogen or complex hydrides. Another means of applying the catalytically active metals to these supports is to impregnate the supports with solutions of thermally readily decomposable salts, for example with nitrates or thermally readily decomposable complexes, for example carbonyl or hydrido complexes of the catalytically active metals, and to heat the thus impregnated support to temperatures in the range from 300 to 600° C. to thermally decompose the adsorbed metal compounds. This thermal decomposition is preferably undertaken under a protective gas atmosphere. Suitable protective gases are, for example, nitrogen, carbon dioxide, hydrogen or the noble gases. In addition, the catalytically active metals may be deposited on the catalyst support by vapor deposition or by flame spraying. The content in the supported catalysts of the catalytically active metals is in principle not critical for the success of the process according to the invention. In general, higher contents of catalytically active metals in the supported catalysts lead to higher space-time conversions than lower contents. In general, supported catalysts are used whose content of catalytically active metals is in the range from 0.1 to 90% by weight, preferably in the range from 0.5 to 40% by weight, based on the total weight of the catalyst. Since these content data are based on the overall catalyst including support material, but the different support materials have very different specific weights and specific surface areas, it is also conceivable for the contents to be lower or higher than these data, without this having a disadvantageous effect on the result of the process according to the invention. It will be appreciated that a plurality of the catalytically active metals may also be applied to the particular support material. In addition, the catalytically active materials may also be applied to the support, for example, by the process of DE-A 25 19 817 or EP 0 285 420 A1. In the catalysts according to the aforementioned documents, the catalytically active metals are present in the form of an alloy which is generated by thermal treatment and/or reduction of the, for example, by impregnation with a salt or complex of the aforementioned metals.

Both the precipitation catalysts and the supported catalysts may also be activated in situ at the start of the reaction by the hydrogen present. Preference is given to separately activating these catalysts before their use.

The support materials used may generally be the oxides of aluminum and of titanium, zirconium dioxide, silicon dioxide, clay minerals, for example montmorillonites, silicates, for example magnesium silicates or aluminum silicates, zeolites, for example of the ZSM-5 or ZSM-10 structure types, or activated carbon. Preferred support materials are aluminas, titanium dioxides, silicon dioxide, zirconium dioxide and activated carbon. It will be appreciated that mixtures of different support materials may also serve as the support for catalysts usable in the process according to the invention.

The at least one heterogeneous catalyst may be used, for example, in the form of a suspension catalyst and/or in the form of a fixed bed catalyst When, for example, the hydrogenation is carried out in the process according to the invention with at least one suspension catalyst, preference is given to hydrogenating in at least one tubular reactor or in at least one bubble column or in at least one packed bubble column or in a combination of two or more identical or different reactors.

The term "different reactors" refers in the present context both to different reactor types and to reactors of the same type which differ, for example, by their geometry, for example their volume and/or their cross section and/or the hydrogenation conditions in the reactors.

When, for example, the hydrogenation is carried out in the process according to the invention with at least one fixed bed catalyst, preference is given to using at least one tubular reactor, for example at least one shaft reactor and/or at least one tube bundle reactor, in which case it is possible to operate a single reactor in liquid phase mode or trickle mode. In the case of use of two or more reactors, at least one may be operated in liquid phase mode and at least one in trickle mode.

In a preferred embodiment of the process according to the invention, the at least one catalyst used for the hydrogenation is removed from the product mixture of the hydrogenation. This removal may be effected, depending upon the catalyst used, in any suitable process version.

When the catalyst used in the hydrogenation is, for example, a heterogeneous catalyst as a suspension catalyst, preference is given in the context of the present invention to removing it by at least one filtration step. The catalyst removed in this way may be recycled into the hydrogenation or fed to at least one arbitrary other process. It is equally possible to work up the catalyst, in order, for example, to recover the metal present in the catalyst.

When the catalyst used in the hydrogenation is, for example, a homogeneous catalyst, preference is given to removing it in the context of the present invention by at least one distillation step. In this distillation, one or two or more distillation columns may be used. The catalyst removed in this way may be recycled into the hydrogenation or fed to at least one arbitrary other process. It is equally possible to work up the catalyst, in order for example, to recover the metal present in the catalyst.

Before use in an arbitrary process, for example before recycling into the process according to the invention, either the at least one homogeneous or the at least one heterogeneous catalyst, can be regenerated should this be necessary by at least one suitable process The heat removal can be realised in the reactor used in accordance with the invention internally, for example via cooling coils, and/or externally, for example via at least one heat exchanger. When, for example and with preference, at least one tubular reactor is used for the hydrogenation, preference is given to conducting the reaction via external circulation, in which the heat removal is integrated.

When, in a preferred embodiment of the process according to the invention, the hydrogenation is carried out continuously, preference is further given to using at least two reactors, more preferably at least two tubular reactors, more preferably at least two serially coupled tubular reactors and especially preferably two serially coupled tubular reactors The hydrogenation conditions in each of the reactors used may be the same or different and are within the above-described ranges.

When the hydrogenation is carried out over at least one suspended catalyst, the residence time is generally in the range from 0.5 to 50 h, preferably in the range form 1 to 30 h and more preferably in the range from 1.5 to 25 h. It is unimportant whether, in accordance with the invention, one reactor or at least two reactors connected in series are used. For all of these embodiments, the overall residence time is within the above-specified ranges.

When, in the process according to the invention, the hydrogenation is carried out in continuous mode over at least one fixed bed catalyst, the residence time is generally in the range from 0.1 to 20 h, preferably in the range from 0.2 to 15 h and more preferably in the range from 0.3 to 10 h. It is unimportant whether, in accordance with the invention, one reactor or at least two reactors connected in series are used. For all of these embodiments, the overall residence time is within the above-specified ranges.

The mixture which is obtained from the first tubular reactor comprises cyclododecanone in a proportion, based on the total content in the mixture of $C_{12}$ components, preferably in the range from 50 to 99.9% by weight and more preferably in the range from 70 to 99.5% by weight. This mixture is, if appropriate after at least one suitable intermediate treatment, fed to the second tubular reactor. The mixture which is obtained from the second tubular reactor comprises cyclododecanone in a proportion preferably in the region of at least 99.5%, more preferably in the region of 99.9% and especially preferably of 99.99% by weight.

The hydrogen pressure in the inventive hydrogenation is generally in the range from 1 to 325 bar, preferably in the range from 1.5 to 200 bar, more preferably in the range from 2 to 100 bar and especially preferably in the range from 2.5 to 50 bar.

The hydrogenation temperature is generally in the range from 0 to 250° C., preferably in the range from 20 to 200° C., more preferably in the range from 30 to 180° C. and especially preferably in the range from 40 to 170° C.

Accordingly, the present invention also relates to a process as described above, wherein the hydrogenation is carried out in the presence of a hydrogenation catalyst, preferably of a heterogeneous hydrogenation catalyst, at a temperature in the range from 0 to 250° C. and a pressure in the range from 1 to 325 bar.

In the context of the inventive hydrogenation, at least one suitable solvent or diluent may be used. Substances suitable as such include cyclododecanone or cyclododecane, and also in principle any solvents and diluents which are not hydrogenated or converted in other ways under the hydrogenation conditions.

In a preferred embodiment of the process according to the invention, the hydrogenation is carried out without addition of a solvent or diluent.

From the inventive hydrogenation, a mixture is generally obtained which, in addition to cyclododecanone, in some cases comprises at least one by-product and/or at least one unconverted reactant and/or at least one further compound which has been fed to the hydrogenation via, for example, a mixture comprising reactant. From this mixture, the cyclododecanone may be removed by at least one suitable method, for example and with preference via at least one distillation.

One of the advantages of the above-described process according to the invention for preparing cyclododecanone is that cyclododecanone and also cyclododecadienone are obtained in few steps and simultaneously with high selectivity A further considerable advantage is the fact that dinitrogen monoxide-containing offgases from preferably industrial plants can be used as a reactant for the process according to the invention, and are firstly available without great cost and inconvenience and secondly enable the integration of the process according to the invention into an existing integrated plant system, which allows the transport path for the reactant to be kept to a minimum, and also, as potential greenhouse gases, do not have to be fed to a special treatment for disposal, but rather flow directly into a product of value.

The cyclododecanone which is obtained with special preference in accordance with the invention and has if appropriate been removed from the product gas mixture may, for example and with particular preference, be used to prepare dodecanedicarboxylic acid and/or laurolactam and/or polymers derived therefrom, for example polyamides such as nylon-12 or nylon-6,12.

The present invention is illustrated by the examples which follow.

EXAMPLES

Example 1

One-Stage Absorption with Tetradecane

A reactant gas (151 mol/h) with the composition specified in table 1.1 is compressed to 25 bar abs., cooled to 30° C. and fed at the lowermost tray of an absorption column (Ø=8 cm, height=400 cm, with Kúhni Rombopak packing). From the top, 96 kg/h of technical-grade tetradecane (coming from the desorber stage) are fed. The depleted offgas at the top of the column is discarded. The laden solvent at the bottom of the absorption column is decompressed in a flash vessel (Ø=20 cm, height=50 cm, operated at 30° C.) to 1 bar abs. The solvent is then pumped back into the absorber stage. The desorbed product gas (12.9 mol/h) is analyzed and discarded. The composition is likewise specified in table 1.1.

TABLE 1.1

| Components | Composition/ % by vol. | |
|---|---|---|
| | Reactant gas | Product gas |
| $N_2O$ | 6.3 | 49 |
| $O_2$ | 4.3 | 2.6 |
| $N_2$ | 87.7 | 44.8 |
| $NO_x$ | 0.05 | 0.16 |
| $CO_2$ | 0.6 | 3.3 |

The formal yield of $N_2O$ (defined as 100×(mol of $N_2O$ in the product gas)/(mol of $N_2O$ in the reactant gas)) is 66%.

Example 2

Two-Stage Absorption with Tetradecane

Example 1 was repeated except that the product gas mixture from the first desorber stage (12.9 mol/h) and with the composition specified in table 1.2 was compressed to 25 bar abs., cooled to 30° C. and fed at the lowermost tray of a second absorption column (Ø=5 cm, height=400 cm, with Kúhni Rombopack packing). From the top, 12 kg/h of technical-grade tetradecane (coming from the second desorber stage) are fed. The depleted offgas at the top of the second absorption column is discarded. The laden solvent at the bottom of the second absorption column is decompressed in a second flash vessel (Ø=10 cm, height=40 cm, operated at 30° C.) to 1 bar abs. The solvent is pymped back into the second absorber stage. The desorbed product gas from the second column (8.8 mol/h) is then analyzed. The composition is likewise specified in table 1.2.

TABLE 1.2

| | Composition/% by vol. | |
|---|---|---|
| Component | 2nd stage reactant gas (= 1st stage product gas) | 2nd stage product gas |
| $N_2O$ | 49 | 88.5 |
| $O_2$ | 2.6 | 0.9 |
| $N_2$ | 44.8 | 1.5 |
| $NO_x$ | 0.16 | 0.4 |
| $CO_2$ | 3.3 | 8.5 |

The formal yield of $N_2O$ (defined as 100×(mol of $N_2O$ in the product gas of the 2nd stage)/(mol of $N_2O$ in the reactant gas of the 1st stage)) is 63%.

Example 3

Two-Stage Absorption with Tetradecane and Subsequent Scrubbing

Example 2 was repeated except that the product gas from the second desorber stage (6.8 mol/h) having the composition specified in table 1.3 was fed to the lowermost tray of a scrubbing column (Ø=5 cm, height=300 cm, with 10 mm Pall rings). From the top, 20 kg/h of an aqueous $NaHCO_3$ solution (concentration: 40 g/kg) are fed. The gas at the top of the scrubbing column is then analyzed. The composition is likewise specified in table 1.3.

TABLE 1.3

| | Composition/% by vol. | |
|---|---|---|
| Component | Scrubbing column reactant gas (= 2nd stage product gas) | Product gas after the scrubbing column |
| $N_2O$ | 88.5 | 87.6 |
| $O_2$ | 0.9 | 0.9 |
| $N_2$ | 1.5 | 1.4 |
| $NO_x$ | 0.4 | 0.1 |
| $CO_2$ | 8.5 | 9.6 |

The formal yield of $N_2O$ (defined as 100×(mol of $N_2O$ in the product gas after the scrubbing column)/(mol of NaO in the reactant gas of the 1st stage)) is 62%.

Example 4

Two-Stage Absorption with Tetradecane with Subsequent Scrubbing and Liquefaction Example 3 was repeated except that the product gas, after the scrubbing column (6.7 mol/h), with the composition specified in table 1.4 was compressed in stages to 25 bar abs. and cooled to −30° C. The condensed product (6.6 mol/h) is then analyzed. The composition is likewise specified in table 1.4.

TABLE 1.4

| | Composition/% by vol. | |
|---|---|---|
| Component | Product gas after the scrubbing column | Liquid product |
| $N_2O$ | 87.6 | 89.1 |
| $O_2$ | 0.9 | 0.1 |
| $N_2$ | 1.4 | 1.2 |
| $NO_x$ | 0.1 | 0.1 |
| $CO_2$ | 9.6 | 8.6 |

The formal yield of $N_2O$ (defined as 100×(mol of $N_2O$ in the liquefied gas)/(mol of $N_2O$ in the reactant gas of the 1st stage)) is 61%.

Example 5

Two-stage Absorption with Nitrobenzene

A reactant gas (150 mol/h) with the composition specified in table 1.5 is compressed to 25 bar, cooled to 30° C. and fed at the lowermost tray of a first absorption column (Ø=8 cm, height=400 cm, with Kúhni Rombopack packing). From the top, 63 kg/h of nitrobenzene (coming from the first desorber stage) are fed. The depleted offgas at the top of the first absorption column is discarded. The laden solvent at the bottom of the first absorption column is decompressed in a flash vessel (Ø=20 cm, height=50 cm, operated at 30° C.) to 1 bar. The solvent is then pumped back into the first absorber stage. The desorbed product gas from the first desorber stage is then compressed to 25 bar, cooled to 30° C. and fed to the lowermost tray of a second absorption column (Ø=5 cm, height=400 cm, with Kúhni Rombopack packing). From the top, 5 kg/h of nitrobenzene (coming from the second desorber stage) are fed. The depleted offgas at the top of the second absorption column is discarded. The laden solvent at the bottom of the second absorption column is decompressed in a second flash vessel (Ø=10 cm, height=40 cm, operated at 30° C.) to 1 bar. The solvent is pumped back into the second absorber stage. The desorbed product from the second column (8.4 mol/h) is then analyzed. The composition is likewise specified in table 1.5.

TABLE 1.5

| | Composition/% by vol. | |
|---|---|---|
| Component | Reactant gas | Product gas |
| $N_2O$ | 9 | 90 |
| $O_2$ | 5.1 | 0.1 |
| $N_2$ | 84.1 | 0.7 |
| $NO_x$ | 0.05 | 0.2 |
| $CO_2$ | 0.87 | 8.7 |

The formal yield of $N_2O$ (defined as 100×(mol of $N_2O$ in the product gas of the 2nd stage)/(mol of $N_2O$ in the reactant gas of the 1st stage)) is 56%.

Example 6

Scrubbing, Two-Stage Absorption with Nitrobenzene, Hydrogencarbonate Scrubbing and Liquefaction A reactant gas (210 mol/h) with the composition specified in table 1.6 is compressed to 4 bar and first washed at 40° C. in a scrubbing column (Ø=8 cm, height=400 cm, with Kúhni Rombopack packing) to which 3.3 kg/h of water are fed. The dilute nitric acid formed is transferred for further utilization. The scrubbed gas is then compressed to 25 bar, cooled to 30° C. and fed at the lowermost tray of the first absorption column (Ø=8 cm, height=400 cm, with Kúhni Rombopack packing). From the top, 73 kg/h of technical-grade nitrobenzene (coming from the first desorber stage) are fed. The depleted offgas at the top of the first absorption column is discarded. The laden solvent at the bottom of the first absorption column is decompressed in a flash vessel (Ø=20 cm, height=50 cm, operated at 30° C.) to 1 bar. The solvent is then pumped back into the first absorber stage. The desorbed product gas from the first desorber stage is then compressed to 25 bar, cooled to 30° C. and fed at the lowermost tray of a second absorption column (Ø=5 cm, height=400 cm, with Kúhni Rombopack packing). From the top, 16 kg/h of technical-grade nitrobenzene (coming from the second desorber stage) are fed. The depleted offgas at the top of the second absorption column is discarded. The laden solvent at the bottom of the second absorption column is decompressed in a second flash vessel (Ø=10 cm, height=40 cm, operated at 30° C.) to 1 bar. The solvent is pumped back into the second absorber stage. The desorbed product gas from the second desorber stage is then fed at lowermost tray of a second scrubbing column (Ø=0.5 cm, height=300 cm, with 10 mm Pail rings). From the top, 24 kg/h of an aqueous $NaHCO_3$ solution (concentration: 40 g/kg) are fed. The gas at the top of the second scrubbing column (34.2 mol/h) is then compressed to 25 bar and cooled to −30° C., and the liquid product is analyzed. The composition is likewise specified in table 1.6.

TABLE 1.6

| Component | Composition/% by vol. | |
|---|---|---|
| | Reactant gas | Liquid product |
| $N_2O$ | 22 | 92.9 |
| $O_2$ | 8.2 | 0.03 |
| $N_2$ | 42.2 | 0.6 |
| $NO_2$ | 22.1 | 0.08 |
| NO | 1 | 0 |
| $CO_2$ | 2.3 | 4.9 |

The formal yield of $N_2O$ (defined as 100×(mol of $N_2O$ in the liquefied gas)/(mol of $N_2O$ in the reactant gas of the 1st stage)) is 69%.

Example 7

From appropriate reservoir vessels, 2000 g/h of cis,trans,trans-1,5,9-cyclododecatriene (of which 200 g/h is fresh and 1800 g/h is recycled reactant) and 73 g/h of a liquid mixture having 93.5% by weight of $N_2O$ are pumped via a static mixer into a tubular reactor (jacketed tube, wound, internal diameter 6 mm, length 36 m). The tube is thermostatted to 280° C. by pumping heat carrier oil in circulation in the jacket. The internal reactor pressure is controlled to 100 bar. After it has passed the reaction zone, the reaction mixture is decompressed in two flash vessels initially to 3 bar and subsequently to 60 mbar, in order to remove the $N_2$ formed, unconverted $N_2O$ and inerts present in the $N_2O$ (mainly $N_3$ and $CO_2$).

The liquid product is then distilled at 60 mbar in a column having at least 7 theoretical plates ($T_{bottom}$=170° C. $T_{top}$=130° C.). The top product obtained is on average 1800 g/h of unconverted cis,trans,trans-1,5,9-cyclododecatriene which is recycled back into the reaction. The bottom effluent which comprises mainly cyclododeca-4,8-dienone is fed into a further column having at least 12 theoretical plates and distilled at 45 mbar. Here, the cyclododeca-4,8-dienone is distilled off overhead as an isomer mixture ($T_{bottom}$=193° C., $T_{top}$=160° C.).

On average, 209 g/h of cyclododeca-4,8-dienone are obtained. The selectivity for cyclododeca-4,8-dienone is 95% (based on cis,trans,trans-1,5,9-cyclododecatriene converted).

What is claimed is:

1. A process for purifying a gas mixture comprising dinitrogen monoxide, comprising:
    A1 absorbing said gas mixture in an organic solvent,
    A2 desorbing said gas mixture from the laden organic solvent, and
    B adjusting the content of nitrogen oxides $NO_x$ in the gas mixture to at most 0.5% by volume based on the total volume of the gas mixture.

2. The process according to claim 1, wherein the gas mixture comprising dinitrogen monoxide is the offgas of at least one plant selected from the group consisting of an adipic acid plant, a dodecanedioic acid plant, a hydroxylamine plant, and a nitric acid plant, wherein the nitric acid plant is operated with the offgas of at least one plant selected from the group consisting of an adipic acid plant, a dodecanedioic acid plant, and a hydroxylamine plant.

3. The process according to claim 1, wherein the organic solvent is selected from the group consisting of toluene, nitrobenzene, 1,2-dichlorobenzene, tetradecane and dimethyl phthalate.

4. The process according to claim 1, wherein A1 and A2 are carried out in a dividing wall column.

5. The process according to claim 1, wherein the process comprises a plurality of A1 and A2.

6. The process according to claim 1, wherein B comprises the absorption of nitrogen oxides in acidic or alkaline solution.

7. The process according to claim 1, wherein A1 and A2 are performed before B.

8. The process according to claim 1, wherein B is performed before A1 and A2.

9. The process according to claim 1, wherein the resulting gas mixture is liquefied.

10. A method of using a gas mixture comprising dinitrogen monoxide as an oxidant for at least one olefin, comprising purifying said gas mixture comprising dinitrogen monoxide, said method comprising:
    A1 absorbing said gas mixture in an organic solvent,
    A2 desorbing said gas mixture from the laden organic solvent, and
    B adjusting the content of nitrogen oxides $NO_x$ in the gas mixture to at most 0.5% by volume based on the total volume of the gas mixture, and then contacting said gas mixture with at least one olefin.

11. A process for preparing a ketone, comprising:
    A1 absorbing a gas mixture comprising dinitrogen monoxide in an organic solvent, A2 desorbing said gas mixture from the laden organic solvent, B adjusting the content of nitrogen oxides $NO_x$ in the gas mixture to at most 0.5% by volume based on the total volume of the gas mixture, and C contacting the gas mixture with at least one olefin.

12. The process according to claim 11, wherein A1 and A2 are performed before B.

13. The process according to claim 11, wherein B is performed before A1 and A2.

14. The process according to claim 11, wherein the gas mixture used in C has been liquefied.

15. The process according to claim 11, wherein the olefin is selected from the group consisting of cyclopentene, cyclododecene and 1,5,9-cyclododecatriene.

16. A process for purifying a gas mixture comprising dinitrogen monoxide, comprising:

A1 absorbing said gas mixture in an organic solvent,

A2 desorbing said gas mixture from the laden organic solvent, and

B adjusting the content of nitrogen oxides $NO_x$ in the gas mixture to at most 0.5% by volume based on the total volume of the gas mixture, wherein the organic solvent is selected from the group consisting of toluene, nitrobenzene, 1,2-dichlorobenzene, tetradecane and dimethyl phthalate.

17. The process according to claim 16, wherein the process comprises a plurality of A1 and A2.

18. The process according to claim 16, wherein B comprises the absorption of nitrogen oxides in acidic or alkaline solution.

19. The process according to claim 16, wherein the resulting gas mixture is liquefied.

20. A method of using a gas mixture comprising dinitrogen monoxide as an oxidant for at least one olefin, comprising purifying said gas mixture comprising dinitrogen monoxide, said method comprising:

A1 absorbing said gas mixture in an organic solvent,

A2 desorbing said gas mixture from the laden organic solvent, and

B adjusting the content of nitrogen oxides $NO_x$ in the gas mixture to at most 0.5% by volume based on the total volume of the gas mixture, wherein the organic solvent is selected from the group consisting of toluene, nitrobenzene, 1,2-dichlorobenzene, tetradecane, and dimethyl phthalate, and then contacting said gas mixture with at least one olefin.

21. A process for preparing a ketone, comprising:

A1 absorbing a gas mixture comprising dinitrogen monoxide in an organic solvent, A2 desorbing said gas mixture from the laden organic solvent, B adjusting the content of nitrogen oxides $NO_x$ in the gas mixture to at most 0.5% by volume based on the total volume of the gas mixture, and C contacting the gas mixture with at least one olefin, wherein the gas mixture used in C has been liquefied.

22. The process according to claim 21, wherein the olefin is selected from the group consisting of cyclopentene, cyclododecene and 1,5,9-cyclododecatriene.

* * * * *